United States Patent
Breitfelder et al.

(10) Patent No.: US 7,041,674 B2
(45) Date of Patent: May 9, 2006

(54) CARBAMIC ACID ESTERS WITH ANTICHOLINERGIC ACTIVITY

(75) Inventors: Steffen Breitfelder, Assmannshardt (DE); Matthias Hoffmann, Mittelbiberach (DE); Matthias Grauert, Biberach (DE); Michael P. Pieper, Biberach (DE); Georg Speck, Ingelheim (DE)

(73) Assignee: Boehringer Ingelhiem Pharma GmbH & Co. KG, Ingelheim (DE)

( * ) Notice: Subject to any disclaimer, the term of this patent is extended or adjusted under 35 U.S.C. 154(b) by 198 days.

(21) Appl. No.: 10/718,403

(22) Filed: Nov. 20, 2003

(65) Prior Publication Data
US 2004/0132760 A1 Jul. 8, 2004

Related U.S. Application Data
(60) Provisional application No. 60/446,600, filed on Feb. 11, 2003.

(30) Foreign Application Priority Data
Nov. 26, 2002 (DE) .......................... 102 55 040

(51) Int. Cl.
*A61K 31/46* (2006.01)
*C07D 491/08* (2006.01)

(52) U.S. Cl. .................. 514/291; 514/295; 514/297; 514/304; 546/91; 546/97; 546/104; 546/105; 546/125; 546/126; 546/127; 546/129; 546/130; 546/131

(58) Field of Classification Search ................ 514/291, 514/295, 297, 304; 546/91, 97, 104, 105, 546/125, 126, 129, 130, 131
See application file for complete search history.

(56) References Cited
U.S. PATENT DOCUMENTS
3,740,405 A   6/1973   Kraft

| | | | | |
|---|---|---|---|---|
| 4,797,387 A | * | 1/1989 | King | 514/213.01 |
| 5,770,738 A | * | 6/1998 | Banholzer et al. | 514/304 |
| 6,113,877 A | * | 9/2000 | Mach et al. | 424/1.65 |

FOREIGN PATENT DOCUMENTS

| | | | |
|---|---|---|---|
| EP | 747355 A1 | * | 12/1996 |
| WO | WO 95 06635 A1 | | 3/1995 |
| WO | WO 97 34892 A1 | | 9/1997 |

OTHER PUBLICATIONS

Banholzer et al. "Preparation of anticholinergic scopine . . ." CA 116:20937 (1992).*
Takeuchi et al. "Preparation of heterocyclyl carbamate . . ." CA 123:849168 (1995).*
Mach et al. "Preparation of azabicycloalkyl . . . " CA 127:307305 (1997).*
Chemical Abstracts: 1995: 849168 HCAPLUS (WO 95 06635).

* cited by examiner

*Primary Examiner*—Celia Chang
(74) *Attorney, Agent, or Firm*—Michael Morris; Mary-Ellen M. Devlin; Andrea D. Small

(57) ABSTRACT

A compound of formula 1

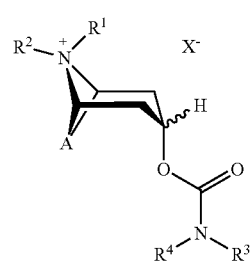

wherein $X^-$, A, $R^1$, $R^2$, $R^3$, and $R^4$ may have the meanings given in the claims and in the specification, processes for preparing them, their use in pharmaceutical compositions, and methods of treating patients using them.

26 Claims, No Drawings

CARBAMIC ACID ESTERS WITH ANTICHOLINERGIC ACTIVITY

RELATED APPLICATIONS

This application claims benefit of U.S. Ser. No. 60/446,600, filed Feb. 11, 2003, and claims priority to German Application No. 102 55 040.9, filed Nov. 26, 2002, each of which is hereby incorporated by reference in its entirety.

FIELD OF THE INVENTION

The present invention relates to new carbamic acid esters of general formula 1

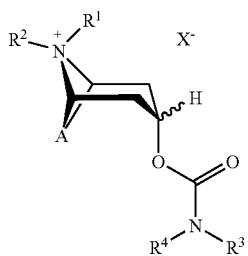

wherein $X^-$ and the groups A, $R^1$, $R^2$, $R^3$, and $R^4$ may have the meanings given in the claims and in the specification, processes for preparing them, and their use as pharmaceutical compositions, particularly as pharmaceutical compositions with an anticholinergic activity.

DESCRIPTION OF THE INVENTION

The present invention relates to compounds of general formula 1

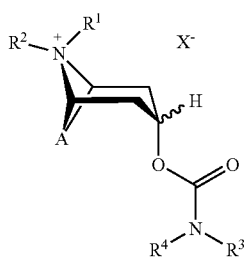

wherein:
A denotes a double-bonded group selected from among

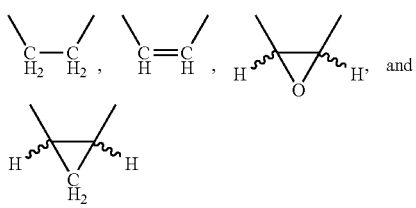
and $X^-$ denotes an anion with a single negative charge, preferably an anion selected from the group consisting of chloride, bromide, iodide, sulfate, phosphate, methanesulfonate, nitrate, maleate, acetate, citrate, fumarate, tartrate, oxalate, succinate, benzoate, and p-toluenesulfonate;

$R^1$ and $R^2$, which may be identical or different, denote $C_1$–$C_5$-alkyl, which is optionally substituted by a group selected from the group consisting of $C_3$–$C_6$-cycloalkyl, hydroxy, or halogen, or $R^1$ and $R^2$ together denote a $C_3$–$C_5$-alkylene bridge; and $R^3$ and $R^4$, which may be identical or different, denote:

(a) hydrogen, or (b) $C_1$–$C_5$-alkyl, which may optionally be mono- or polysubstituted by one or more groups selected from the group consisting of hydroxy, halogen, —$CF_3$, and —$OC_1$–$C_4$-alkyl, or (c) a $C_2$–$C_5$-alkenyl or $C_2$–$C_5$-alkynyl group, which may optionally be mono- or polysubstituted by one or more groups selected from the group consisting of hydroxy, halogen, —$CF_3$, —$OC_1$–$C_4$-alkyl, phenyl, and phenyl which may be mono- or polysubstituted by methyl, halogen, hydroxy, —$CF_3$, or methoxy, or (d) $C_6$–$C_{10}$-aryl, which may optionally be substituted by one or more groups selected from the group consisting of $C_1$–$C_4$-alkyl, hydroxy, halogen, —$CF_3$, —$OC_1$–$C_4$-alkyl, phenyl, and phenyl which may be mono- or polysubstituted by methyl, halogen, hydroxy, —$CF_3$, or methoxy, or (e) $C_6$–$C_{10}$-aryl, which is substituted by a 5- or 6-membered heteroaryl ring, which may optionally be mono- or polysubstituted by methyl, halogen, hydroxy, —$CF_3$, or methoxy, or (f) $C_6$–$C_{10}$-aryl-$C_1$–$C_4$-alkylene, which may optionally be substituted at the aryl group by one or more groups selected from the group consisting of $C_1$–$C_4$-alkyl, hydroxy, halogen, —$CF_3$, —$OC_1$–$C_4$-alkyl, phenyl, and phenyl which may be mono- or polysubstituted by methyl, halogen, hydroxy, —$CF_3$, or methoxy, or (g) $C_6$–$C_{10}$-aryl-$C_1$–$C_4$-alkylene, which is substituted at the aryl group by a 5- or 6-membered heteroaryl ring, which may optionally be mono- or polysubstituted by methyl, halogen, hydroxy, —$CF_3$, or methoxy, or (h) $C_6$–$C_{10}$-aryl-$C_1$–$C_4$-alkylene, which may optionally be substituted at the alkylene group by one or more groups selected from the group consisting of $C_1$–$C_4$-alkyl, hydroxy, halogen, —$CF_3$, —$OC_1$–$C_4$-alkyl, and phenyl, or (i) a 5- or 6-membered saturated or unsaturated ring which may contain one, two, or three heteroatoms selected from the group consisting of nitrogen, oxygen, or sulfur, and which may optionally be mono- or polysubstituted by one or more groups selected from the group consisting of $C_1$–$C_4$-alkyl hydroxy, halogen, —$CF_3$, phenyl, benzyl, and —$OC_1$–$C_4$-alkyl, or (j) a 5- or 6-membered saturated or unsaturated ring which may contain one, two, or three heteroatoms selected from the group consisting of nitrogen, oxygen, or sulfur, and which is substituted by a 5- or 6-membered heteroaryl ring, which may optionally be mono- or polysubstituted by methyl, halogen, hydroxy, —$CF_3$, or methoxy, or (k) $C_3$–$C_6$-cycloalkyl, which may optionally be substituted by one or more groups selected from the group consisting of $C_1$–$C_4$-alkyl, hydroxy, halogen, —$CF_3$, —$OC_1$–$C_4$-alkyl, phenyl, and phenyl which may be mono- or polysubstituted by methyl, halogen, hydroxy, —$CF_3$, or methoxy, or (l) $C_3$–$C_6$-cycloalkyl, which is substituted by a 5- or 6-membered heteroaryl ring, which may optionally be mono- or polysubstituted by methyl, halogen, hydroxy, —$CF_3$, or methoxy, or (m) a group of formula

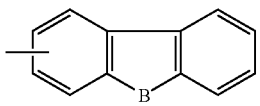

wherein B denotes —CH$_2$—, —NH—, —S—, or —O—, which may optionally be mono- or polysubstituted by one or more groups selected from the group consisting of C$_1$–C$_4$-alkyl, hydroxy, halogen, —CF$_3$, and —OC$_1$–C$_4$-alkyl, or (n) a group of formula

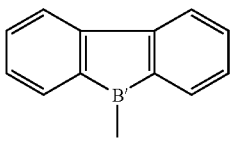

wherein B' denotes CH or N, which may optionally be mono- or polysubstituted by one or more groups selected from the group consisting of C$_1$–C$_4$-alkyl, hydroxy, halogen, —CF$_3$, and —OC$_1$–C$_4$-alkyl, or (o) a group of formula

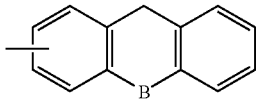

wherein B denotes —CH$_2$—, —NH—, —S—, or —O—, which may optionally be mono- or polysubstituted by one or more groups consisting of C$_1$–C$_4$-alkyl, hydroxy, halogen, —CF$_3$, and —OC$_1$–C$_4$-alkyl, or (p) a group of formula

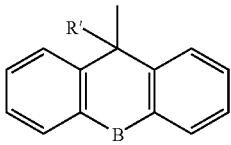

wherein B denotes —CH$_2$—, —NH—, —S—, or —O—, and

R' may represent hydrogen, hydroxy, methyl, hydroxymethyl, ethyl, —CF$_3$, —CHF$_2$, or halogen, and which may optionally be mono- or polysubstituted by one or more groups selected from the group consisting of C$_1$–C$_4$-alkyl, hydroxy, halogen, —CF$_3$, and —OC$_1$–C$_4$-alkyl, or R$^3$ and R$^4$ together with the nitrogen atom form a 5- or 6-membered saturated or unsaturated heterocyclic ring which may optionally contain one or two more heteroatoms selected from the group consisting of nitrogen, oxygen, or sulfur, and which may optionally be mono- or polysubstituted by one or more groups selected from the group consisting of C$_1$–C$_4$-alkyl hydroxy, halogen, —CF$_3$, phenyl, benzyl, and —OC$_1$–C$_4$-alkyl, or R$^3$ and R$^4$ together with the nitrogen atom form a 5- or 6-membered saturated or unsaturated heterocyclic ring which is substituted by a 5- or 6-membered heteroaryl ring, which may optionally be mono- or polysubstituted by methyl, halogen, hydroxy, —CF$_3$, or methoxy, optionally in the form of the individual enantiomers or diastereomers, mixtures of the enantiomers or diastereomers and optionally in the form of the racemates, and optionally in the form of the pharmacologically acceptable acid addition salts, solvates and hydrates thereof.

Preferred are compounds of general formula 1 wherein:

A denotes a double-bonded group selected from among

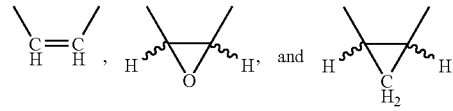

X$^-$ denotes an anion with a single negative charge, preferably an anion selected from the group consisting of chloride, bromide, methanesulfonate, and p-toluenesulfonate, preferably bromide;

R$^1$ and R$^2$, which may be identical or different, denote C$_1$–C$_3$-alkyl, which may optionally be substituted by a group selected from the group consisting of C$_3$–C$_5$ cycloalkyl, hydroxy, or fluorine, or R$^1$ and R$^2$ together denote a C$_3$–C$_4$-alkylene bridge; and R$^3$ and R$^4$, which may be identical or different, denote (a) hydrogen, or (b) C$_1$–C$_5$-alkyl, which may optionally be substituted by a group selected from the group consisting of hydroxy, fluorine, —CF$_3$, and methoxy, or (c) a phenyl or naphthyl group which may optionally be substituted by one, two, or three groups selected from the group consisting of methyl, ethyl, hydroxy, fluorine, chlorine, bromine, —CF$_3$, methoxy, phenyl, and phenyl which may be mono-, di-, or trisubstituted by methyl, fluorine, chlorine, bromine, hydroxy, —CF$_3$, or methoxy, or (d) a phenyl or naphthyl group which is substituted by a heteroaryl ring selected from the group consisting of furan, thiophene, pyrrole, imidazole, pyridine, and pyrimidine, which may optionally be mono- or disubstituted by methyl, fluorine, chlorine bromine, hydroxy, —CF$_3$, or methoxy, or (e) a benzyl or phenylethyl group which may optionally be substituted at the phenyl ring by one, two, or three groups selected from the group consisting of methyl, ethyl, hydroxy, fluorine, chlorine, bromine, —CF$_3$, methoxy, phenyl, and phenyl which may be mono-, di-, or trisubstituted by methyl, fluorine, chlorine, bromine, hydroxy, —CF$_3$, or methoxy, or (f) a benzyl or phenylethyl group which is substituted at the phenyl ring by a heteroaryl ring selected from the group consisting of furan, thiophene, pyrrole, imidazole, pyridine, and pyrimidine, which may optionally be mono- or disubstituted by methyl, fluorine, chlorine bromine, hydroxy, —CF$_3$, or methoxy, or (g) a benzyl or phenylethyl group which may optionally be substituted at the alkylene bridge by one or two, preferably one group selected from the group consisting of methyl, ethyl, hydroxy, fluorine, chlorine, bromine, —CF$_3$, methoxy, and phenyl, or (h) a 5- or 6-membered saturated or unsaturated ring which may contain one, two, or three heteroatoms selected from the group consisting of nitrogen, oxygen, or sulfur, and which may optionally be mono-, di-, or trisubstituted by one or more groups selected from the group consisting of methyl, ethyl, hydroxy, fluorine, chlorine, bromine, —CF$_3$, phenyl, benzyl, and methoxy, or (i) a 5- or 6-membered saturated or unsaturated ring which may contain one, two, or three heteroatoms selected from the group consisting of nitrogen, oxygen, or sulfur, and which is substituted by a heteroaryl ring selected from the group consisting of furan, thiophene, pyrrole, imidazole, pyridine, and pyrimidine, which may optionally be mono- or disubstituted by methyl, fluorine, chlorine bromine, hydroxy, —$CF_3$, or methoxy, or (l) a cyclopentyl or cyclohexyl group which may optionally be substituted by one, two, or three groups selected from the group consisting of methyl, ethyl, hydroxy, fluorine, chlorine, bromine, —$CF_3$, methoxy, phenyl, and phenyl which may be mono-, di-, or trisubstituted by methyl, fluorine, chlorine, bromine, hydroxy, —$CF_3$, or methoxy, or (k) a cyclopentyl or cyclohexyl group which is substituted by a heteroaryl ring selected from the group consisting of furan, thiophene, pyrrole, imidazole, pyridine, and pyrimidine, which may optionally be mono- or disubstituted by methyl, fluorine, chlorine bromine, hydroxy, —$CF_3$, or methoxy, or (l) a group of formula

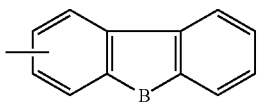

wherein B denotes —$CH_2$—, —NH—, —S—, or —O—, which may optionally be mono-, di-, or trisubstituted by one or more groups selected from the group consisting of methyl, fluorine, chlorine, bromine, hydroxy, —$CF_3$, or methoxy, or (m) a group of formula

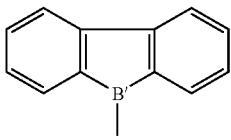

wherein B' denotes CH or N, which may optionally be mono-, di-, or trisubstituted by one or more groups selected from the group consisting of methyl, fluorine, chlorine, bromine, hydroxy, —$CF_3$, or methoxy, or (n) a group of formula

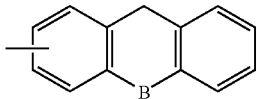

wherein B denotes —$CH_2$—, —NH—, —S—, or —O—, which may optionally be mono-, di-, or trisubstituted by one or more groups selected from the group consisting of methyl, fluorine, chlorine, bromine, hydroxy, —$CF_3$, or methoxy, or (o) a group of formula

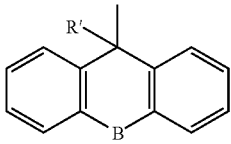

wherein B denotes —$CH_2$—, —NH—, —S—, or —O—, and

R' may represent hydrogen, hydroxy, methyl, hydroxymethyl, ethyl, —$CF_3$, —$CHF_2$, or fluorine, and which may optionally be mono-, di-, or trisubstituted by one or more groups selected from the group consisting of methyl, fluorine, chlorine, bromine, hydroxy, —$CF_3$, or methoxy, or $R^3$ and $R^4$ together with the nitrogen atom form a 5- or 6-membered saturated or unsaturated heterocyclic ring which may optionally contain one or two more heteroatoms selected from the group consisting of nitrogen, oxygen, or sulfur, and which may optionally be mono-, di-, or trisubstituted by one or more groups selected from the group consisting of methyl, fluorine, chlorine, bromine, hydroxy, phenyl, —$CF_3$, or methoxy, or $R^3$ and $R^4$ together with the nitrogen atom form a 5- or 6-membered saturated or unsaturated heterocyclic ring which may optionally contain one or two more heteroatoms selected from the group consisting of nitrogen, oxygen, or sulfur, which is substituted by a heteroaryl ring selected from the group consisting of furan, thiophene, pyrrole, imidazole, pyridine, and pyrimidine, which may optionally be mono- or disubstituted by methyl, fluorine, chlorine bromine, hydroxy, —$CF_3$, or methoxy, optionally in the form of the individual enantiomers or diastereomers, mixtures of the enantiomers or diastereomers and optionally in the form of the racemates, and optionally in the form of the pharmacologically acceptable acid addition salts, solvates and hydrates thereof.

Particularly preferred are compounds of general formula 1 wherein:

A denotes a double-bonded group selected from among

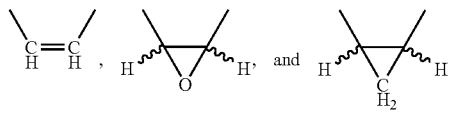

$X^-$ denotes an anion with a single negative charge, preferably an anion selected from the group consisting of chloride, bromide, methanesulfonate, and p-toluenesulfonate, preferably bromide;

$R^1$ and $R^2$, which may be identical or different, denote a methyl or ethyl group which may optionally be substituted by cyclopropyl, hydroxy, or fluorine, or $R^1$ and $R^2$ together denote a $C_3$–$C_4$-alkylene bridge;

$R^3$ denotes hydrogen or $C_1$–$C_3$-alkyl, which may optionally be substituted by a group selected from the group consisting of hydroxy, fluorine, or —$CF_3$;

$R^4$ denotes $C_1$–$C_3$-alkyl, which may optionally be substituted by a group selected from the group consisting of hydroxy, fluorine, or —$CF_3$;

$R^4$ denotes a phenyl group which may optionally be substituted by one or two, preferably one group selected from the group consisting of furyl, thienyl, phenyl, and phenyl which may be mono-, di-, or trisubstituted by methyl, fluorine, chlorine, bromine, hydroxy, —$CF_3$, or methoxy, or $R^4$ denotes a benzyl group which may optionally be substituted at the phenyl ring by one, two, or three, preferably one group selected from the group consisting of methyl, ethyl, hydroxy, fluorine, chlorine, bromine, —$CF_3$, methoxy, furyl, thienyl, and phenyl, or $R^4$ denotes a benzyl group which may optionally be substituted at the methylene bridge by one, two, or three, preferably one group selected from the group consisting of methyl, ethyl, hydroxy, fluorine, chlorine, bromine, —$CF_3$, methoxy, and phenyl, or $R^4$ denotes a group of formula

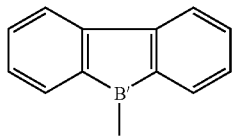

wherein B' denotes CH, which may optionally be mono- or disubstituted by one or more groups selected from the group consisting of methyl, fluorine, chlorine, bromine, hydroxy, —$CF_3$, or methoxy,
optionally in the form of the individual enantiomers or diastereomers, mixtures of the enantiomers or diastereomers and optionally in the form of the racemates, and optionally in the form of the pharmacologically acceptable acid addition salts, solvates and hydrates thereof.

Also of particular interest are compounds of general formula 1 wherein:
A denotes a double-bonded group selected from among:

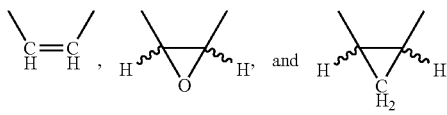

$X^-$ denotes an anion with a single negative charge selected from the group consisting of chloride, bromide, methanesulfonate, and p-toluenesulfonate, preferably bromide;

$R^1$ and $R^2$, which may be identical or different, denote a methyl or ethyl group which may optionally be substituted by cyclopropyl, hydroxy, or fluorine, or $R^1$ and $R^2$ together denote a $C_3$–$C_4$-alkylene bridge;

$R^3$ denotes hydrogen or $C_1$–$C_3$-alkyl, which may optionally be substituted by a group selected from the group consisting of hydroxy, fluorine, or —$CF_3$; and $R^4$ denotes $C_1$–$C_3$-alkyl, which may optionally be substituted by a group selected from the group consisting of hydroxy, fluorine, or —$CF_3$, $R^4$ denotes a phenyl group which may optionally be substituted by phenyl, which may optionally be mono- or disubstituted by methyl, fluorine, hydroxy, or —$CF_3$, or $R^4$ denotes a benzyl group which may optionally be substituted at the phenyl ring by one or two, preferably one group selected from the group consisting of methyl, ethyl, hydroxy, fluorine, —$CF_3$, and phenyl, or $R^4$ denotes a benzyl group which may optionally be monosubstituted at the methylene bridge by phenyl, or $R^4$ denotes a group of formula

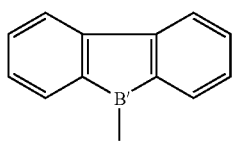

wherein B' denotes CH, which may optionally be mono- or disubstituted by one or more groups selected from the group consisting of methyl, fluorine, chlorine, bromine, hydroxy, —$CF_3$, or methoxy,
optionally in the form of the individual enantiomers or diastereomers, mixtures of the enantiomers or diastereomers and optionally in the form of the racemates, and optionally in the form of the pharmacologically acceptable acid addition salts, solvates, and hydrates thereof.

Of the abovementioned compounds of general formula 1, particular importance is attached to those wherein $X^-$ denotes bromide or methanesulfonate, most preferably bromide, optionally in the form of the individual enantiomers or diastereomers, mixtures of the enantiomers or diastereomers and optionally in the form of the racemates, and optionally in the form of the pharmacologically acceptable acid addition salts, solvates and hydrates thereof.

Also particularly preferred according to the invention, are those of the above-mentioned compounds of formula 1 wherein $R^1$ and $R^2$ have the same meaning and denote methyl, optionally in the form of the individual enantiomers or diastereomers, mixtures of the enantiomers or diastereomers and optionally in the form of the racemates, and optionally in the form of the pharmacologically acceptable acid addition salts, solvates, and hydrates thereof.

Also of particular importance according to the invention, are those of the abovementioned compounds of formula 1, wherein $R^3$ denotes hydrogen or methyl, optionally in the form of the individual enantiomers or diastereomers, mixtures of the enantiomers or diastereomers and optionally in the form of the racemates, and optionally in the form of the pharmacologically acceptable acid addition salts, solvates, and hydrates thereof.

Also of particular importance are all the compounds of general formula 1 wherein the group $R^4$ denotes biphenyl, benzhydryl, fluorenyl, or biphenylmethyl, optionally in the form of the individual enantiomers or diastereomers, mixtures of the enantiomers or diastereomers and optionally in the form of the racemates, and optionally in the form of the pharmacologically acceptable acid addition salts, solvates, and hydrates thereof.

Of outstanding importance according to the invention are compounds of general formula 1 wherein:
A denotes a double-bonded group selected from among:

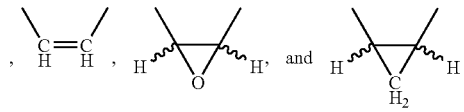

$X^-$ denotes an anion with a single negative charge, preferably an anion selected from the group consisting of bromide and methanesulfonate, preferably bromide;

$R^1$ and $R^2$ denote methyl;

$R^3$ denotes hydrogen or methyl; and $R^4$ denotes biphenyl, benzhydryl, fluorenyl, or biphenylmethyl,
optionally in the form of the individual enantiomers or diastereomers, mixtures of the enantiomers or diastereomers and optionally in the form of the racemates, and optionally in the form of the pharmacologically acceptable acid addition salts, solvates, and hydrates thereof.

The alkyl groups used, unless otherwise stated, are branched and unbranched alkyl groups having 1 to 5 carbon atoms. Examples include: methyl, ethyl, propyl, or butyl. The groups methyl, ethyl, propyl, or butyl may optionally also be referred to by the abbreviations Me, Et, Prop, or Bu. Unless otherwise stated, the definitions propyl and butyl also include all possible isomeric forms of the groups in question. Thus, for example, propyl includes n-propyl and isopropyl, butyl includes isobutyl, sec-butyl, and tert-butyl, etc.

The alkylene groups used, unless otherwise stated, are branched and unbranched double-bonded alkyl bridges with 1 to 5 carbon atoms. Examples include: methylene, ethylene, n-propylene, or n-butylene.

The alkyloxy groups used, unless otherwise stated, are branched and unbranched alkyl groups with 1 to 4 carbon atoms which are linked via an oxygen atom. The following may be mentioned, for example: methyloxy, ethyloxy, propyloxy, or butyloxy. The groups methyloxy, ethyloxy, propyloxy, or butyloxy may optionally also be referred to by the abbreviations MeO, EtO, PropO, or BuO. Unless otherwise stated, the definitions propyloxy and butyloxy also include all possible isomeric forms of the groups in question. Thus, for example, propyloxy includes n-propyloxy and isopropyloxy, butyloxy includes isobutyloxy, sec-butyloxy, and tert-butyloxy, etc. The word alkoxy may also possibly be used within the scope of the present invention instead of the word alkyloxy. The groups methyloxy, ethyloxy, propyloxy, or butyloxy may optionally also be referred to as methoxy, ethoxy, propoxy, or butoxy.

Within the scope of the present invention halogen denotes fluorine, chlorine, bromine, or iodine. Unless otherwise stated, fluorine and bromine are the preferred halogens.

The alkenyl groups used are branched and unbranched hydrocarbon groups with 2 to 5 carbon atoms, preferably 2 to 3 carbon atoms, provided that they have at least one double bond. Examples include vinyl, propenyl, isopropenyl, butenyl, butadienyl, and pentenyl.

The alkynyl groups used are hydrocarbon groups with 2 to 5 carbon atoms, provided that they have at least one triple bond, for example, ethynyl, propargyl, butynyl, and pentynyl.

The term aryl denotes an aromatic ring system with 6 to 10 carbon atoms. Preferred aryl. groups are phenyl or naphthyl.

By 5- or 6-membered heteroaryl rings are meant, within the scope of the present invention, aromatic ring systems which contain one or two heteroatoms selected from the group consisting of oxygen, nitrogen, and sulfur, and may optionally be substituted as defined hereinbefore. Examples include furan, thiophene, pyrrole, pyrazole, imidazole, pyridine, pyrimidine, triazine, oxazole, isoxazole, thiazole, isothiazole, oxadiazole, and pyrazolidine, while the heterocycle may be substituted as specified in the definitions. Particularly preferred 5- or 6-membered heterocyclic rings within the scope of the present invention are furan, thiophene, pyrrole, imidazole, pyridine, and pyrimidine, while furan and thiophene are particularly important.

The term arylalkylene denotes aromatic ring systems with 6 to 10 carbon atoms which are linked via an alkylene bridge with 1–4 carbon atoms. Examples of arylalkylene groups include benzyl or phenylethyl.

Examples of 5- or 6-membered saturated or unsaturated heterocyclic rings which may contain nitrogen, oxygen, or sulfur as heteroatoms include furan, tetrahydrofuran, 2-methyltetrahydrofuran, 2-hydroxymethylfuran, tetrahydrofuranone, γ-butyrolactone, α-pyran, γ-pyran, dioxolane, tetrahydropyran, dioxane, thiophene, dihydrothiophene, thiolane, dithiolane, pyrrole, pyrroline, pyrrolidine, pyrazole, pyrazoline, imidazole, imidazoline, imidazolidine, triazole, tetrazole, pyridine, piperidine, pyridazine, pyrimidine, pyrazine, piperazine, triazine, tetrazine, morpholine, thiomorpholine, oxazole, isoxazole, oxazine, thiazole, isothiazole, thiadiazole, oxadiazole, and pyrazolidine, while the heterocyclic group may be substituted as in the definitions. Particularly preferred 5- or 6-membered heterocyclic rings within the scope of the present invention are furan, thiophene, pyrrole, imidazole, pyridine, piperidine, pyrimidine, morpholine, oxazole, and oxadiazole, while the furan, thiophene, pyrrole, imidazole, pyridine, and piperidine rings are particularly important according to the invention.

Examples of cycloalkyl groups with 3–6 carbon atoms include, for example, cyclopropyl, cyclobutyl, cyclopentyl, or cyclohexyl.

Examples of 5-, 6-, or 7-membered saturated or unsaturated heterocyclic rings which may be formed by the groups $R^3$ and $R^4$ together with the nitrogen include: pyrrole, pyrroline, pyrrolidine, 2-methylpyrrolidine, 3-methylpyrrolidine, piperidine, piperazine, N-methylpiperazine, N-ethylpiperazine, N-(n-propyl) piperazine, N-benzylpiperazine, morpholine, thiomorpholine, imidazole, imidazoline, imidazolidine, pyrazole, pyrazoline, and pyrazolidine, preferably morpholine, N-benzylpiperazine, piperazine, and piperidine, while the abovementioned heterocycles may be substituted as in the definitions. Particularly preferred rings in this context are: pyrrole, piperidine, piperazine, N-methylpiperazine, N-benzylpiperazine, morpholine, imidazole, imidazoline, imidazolidine, pyrazole, pyrazoline, pyrazolidine, preferably morpholine, N-benzylpiperazine, piperazine, and piperidine, while the abovementioned heterocycles may be substituted as in the definitions.

By pharmacologically acceptable acid addition salts are meant, for example, the salts selected from the group consisting of hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate.

The compounds according to the invention may in some cases be prepared analogously to the methods known from the prior art, as explained hereinafter. Scheme 1 illustrates the method of synthesizing compounds of formula 1 wherein $R^3$ denotes hydrogen.

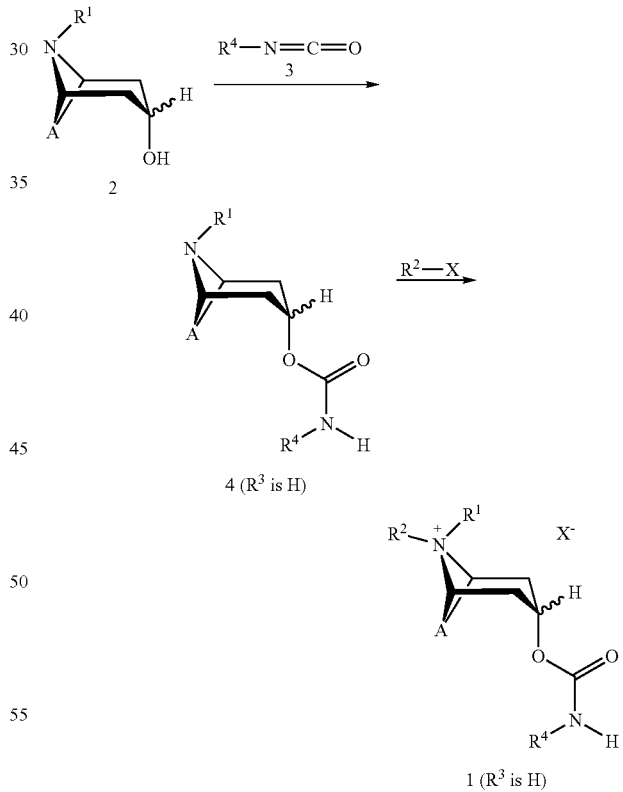

These compounds may be obtained starting from the alcohols of formula 2 by reacting with the isocyanates of formula 3. The isocyanates of formula 3 are known in the prior art or may be prepared using methods of synthesis known from the prior art. If desired, the isocyanates of formula 3 may be generated in situ using methods known from the prior art and used in the reaction without any further isolation. The compounds of formula 2 are also known in the prior art. The reaction of the compounds 2 with the isocyanates 3 is preferably carried out in an aprotic organic solvent, particularly preferably in an aprotic polar solvent selected, for example, from the group consisting of acetonitrile, tetrahydrofuran, and dioxane, preferably acetonitrile, at temperatures from 0° C.–100° C., preferably at about 10° C.–50° C., most preferably at ambient temperature (about 23° C.). The working up of the reaction mixture and the purification of the intermediate product 4 are carried out using conventional methods. Compounds of formula 4 wherein $R^3$ denotes hydrogen are partly known from the prior art. In connection-with this, reference is made to the publications WO 97/34892, Aberle et al. (Tetrahedron Letters 42 (2001) 1975–1977) as well as Polonovski et al. (Bull. Soc. Chim. Fr. <4>43, 1928, 596), which are each incorporated by reference.

The compounds of formula 1 wherein $R^3$ does not represent hydrogen may be obtained as shown in Scheme 2.

Scheme 2

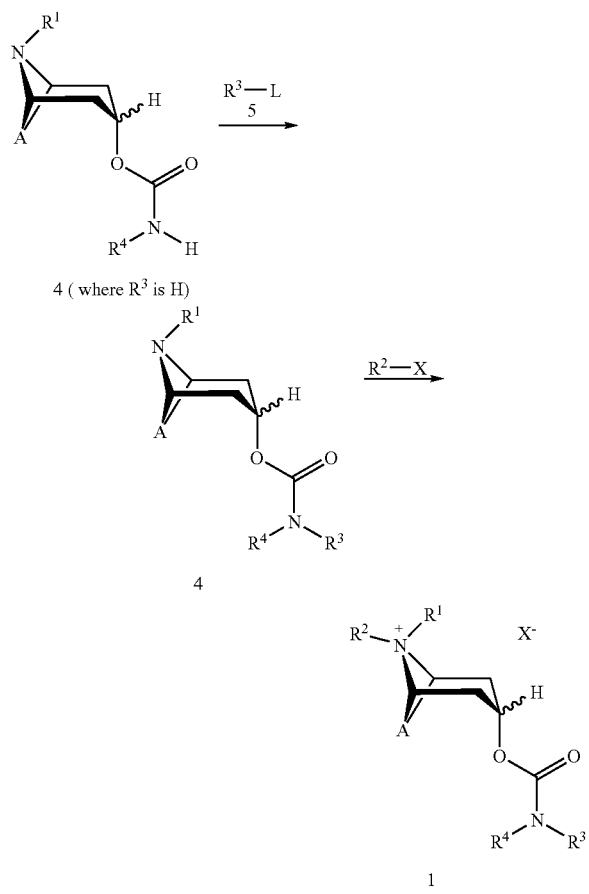

4

For this reaction, a compound of formula 4 wherein $R^3$ denotes hydrogen, is reacted with the compound 5 in a suitable organic solvent in the presence of a strong base. In compound 5, $R^3$ may have the above meanings. L denotes a leaving group, preferably a leaving group selected from chlorine, bromine, iodine, mesylate, triflate, benzenesulfonate, or tosylate. According to the invention, alkali metal hydrides are preferably used as bases. The hydrides of sodium, lithium, and potassium are preferred. Suitable solvents are preferably selected from dimethylformamide, dimethylacetamide, methylene chloride, and tetrahydrofuran. The reaction mixture is reacted for 0.5 to 4 days, preferably 1 to 2 days at ambient temperature, optionally also at elevated temperature. The working up of the reaction mixture and purification of the product 4 are carried out by conventional methods.

The compounds of formula 4 obtained according to Scheme 1 or Scheme 2 may be converted into the target compounds of formula 1 by reacting with the compounds $R^2$—X, wherein $R^2$ and X may have the above meanings. This synthesizing step may also be carried out analogously to the examples of synthesis disclosed in WO 92/16528. In the event that $R^1$ and $R^2$ together form an alkylene bridge, there is no need to add the reagent $R^2$—X, as will be apparent to anyone skilled in the art. In this case, the compounds of formula 4 have a suitably substituted group $R^1$ (—$C_3$–$C_5$-alkylene-X) corresponding to the abovementioned definitions and the compounds of formula 1 are prepared by intramolecular quaternization of the amine.

As can be seen from Scheme 1, the intermediate products of general formula 4 are of central importance. Accordingly, in another aspect, the present invention relates to the intermediates of formula 4

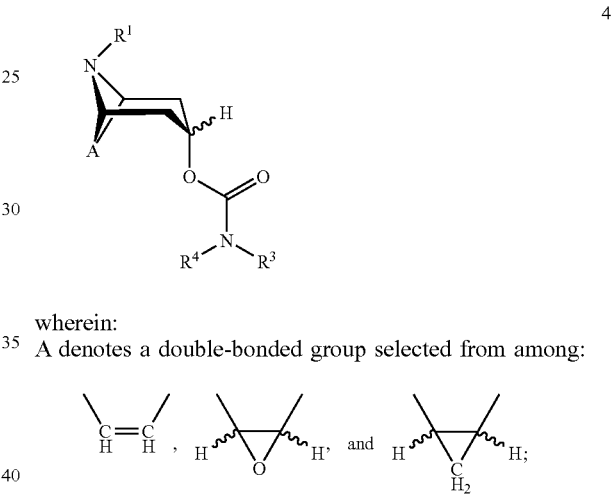

4 wherein:

A denotes a double-bonded group selected from among:

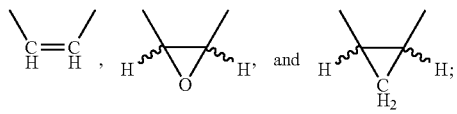

$R^1$ denotes $C_1$–$C_5$-alkyl, which may optionally be substituted by a group selected from the group consisting of $C_3$–$C_6$-cycloalkyl or hydroxy, or $R^1$ denotes —$C_3$–$C_5$-alkylene-X, wherein X denotes chloride, bromide, iodide, sulfate, phosphate, methanesulfonate, nitrate, maleate, acetate, citrate, fumarate, tartrate, oxalate, succinate, benzoate, and p-toluenesulfonate;

$R^3$ and $R^4$, which may be identical or different, denote
(a) hydrogen, or
(b) $C_1$–$C_5$-alkyl, which may optionally be mono- or polysubstituted by one or more groups selected from the group consisting of hydroxy, halogen, —$CF_3$, and —$OC_1$–$C_4$-alkyl, or
(c) a $C_2$–$C_5$-alkenyl or $C_2$–$C_5$-alkynyl group, which may optionally be mono- or polysubstituted by one or more groups selected from the group consisting of hydroxy, halogen, —$CF_3$, —$OC_1$–$C_4$-alkyl, phenyl, and phenyl which may be mono- or polysubstituted by methyl, halogen, hydroxy, —$CF_3$, or methoxy, or
(d) $C_6$–$C_{10}$-aryl, which may optionally be substituted by one or more groups selected from the group consisting of $C_1$–$C_4$-alkyl, hydroxy, halogen, —$CF_3$, —$OC_1$–$C_4$-alkyl, phenyl, and phenyl which may be mono- or polysubstituted by methyl, halogen, hydroxy, —$CF_3$, or methoxy, or (e) C$_6$–C$_{10}$-aryl, which is substituted by a 5- or 6-membered heteroaryl ring, which may optionally be mono- or polysubstituted by methyl, halogen, hydroxy, —CF$_3$, or methoxy, or (f) C$_6$–C$_{10}$-aryl-C$_1$–C$_4$-alkylene, which may optionally be substituted at the aryl group by one or more groups selected from the group consisting of C$_1$–C$_4$-alkyl, hydroxy, halogen, —CF$_3$, —OC$_1$–C$_4$-alkyl, phenyl, and phenyl which may be mono- or polysubstituted by methyl, halogen, hydroxy, —CF$_3$, or methoxy, or (g) C$_6$–C$_{10}$-aryl-C$_1$–C$_4$-alkylene, which is substituted at the aryl group by a 5- or 6-membered heteroaryl ring, which may optionally be mono- or polysubstituted by methyl, halogen, hydroxy, —CF$_3$, or methoxy, or (h) C$_6$–C$_{10}$-aryl-C$_1$–C$_4$-alkylene, which may optionally be substituted at the alkylene group by one or more groups selected from the group consisting of C$_1$–C$_4$-alkyl, hydroxy, halogen, —CF$_3$, —OC$_1$–C$_4$-alkyl, and phenyl, or (i) a 5- or 6-membered saturated or unsaturated ring which may contain one, two, or three heteroatoms selected from the group consisting of nitrogen, oxygen, or sulfur, and which may optionally be mono- or polysubstituted by one or more groups selected from the group consisting of C$_1$–C$_4$-alkyl hydroxy, halogen, —CF$_3$, phenyl, benzyl, and —OC$_1$–C$_4$-alkyl, or (j) a 5- or 6-membered saturated or unsaturated ring which may contain one, two, or three heteroatoms selected from the group consisting of nitrogen, oxygen, or sulfur, and which is substituted by a 5- or 6-membered heteroaryl ring, which may optionally be mono- or polysubstituted by methyl, halogen, hydroxy, —CF$_3$, or methoxy, or (k) C$_3$–C$_6$-cycloalkyl, which may optionally be substituted by one or more groups selected from the group consisting of C$_1$–C$_4$-alkyl, hydroxy, halogen, —CF$_3$, —OC$_1$–C$_4$-alkyl, phenyl, and phenyl which may be mono- or polysubstituted by methyl, halogen, hydroxy, —CF$_3$, or methoxy, or (l) C$_3$–C$_6$-cycloalkyl, which is substituted by a 5- or 6-membered heteroaryl ring, which may optionally be mono- or polysubstituted by methyl, halogen, hydroxy, —CF$_3$, or methoxy, or (m) a group of formula

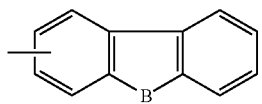

wherein B denotes —CH$_2$—, —NH—, —S—, or —O—, which may optionally be mono- or polysubstituted by one or more groups selected from the group consisting of C$_1$–C$_4$-alkyl, hydroxy, halogen, —CF$_3$, and —OC$_1$–C$_4$-alkyl, or (n) a group of formula

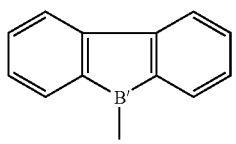

wherein B' denotes CH or N, which may optionally be mono- or polysubstituted by one or more groups selected from the group consisting of C$_1$–C$_4$-alkyl, hydroxy, halogen, —CF$_3$, and —C$_1$–C$_4$-alkyl, or (o) a group of formula

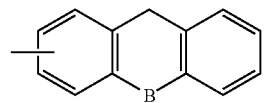

wherein B denotes —CH$_2$—, —NH—, —S—, or —O—, which may optionally be mono- or polysubstituted by one or more groups selected from the group consisting of C$_1$–C$_4$-alkyl, hydroxy, halogen, —CF$_3$, and —OC$_1$–C$_4$-alkyl, or (p) a group of formula

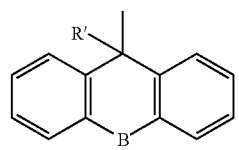

wherein B denotes —CH$_2$—, —NH—, —S—, or —O—, and

R' may represent hydrogen, hydroxy, methyl, hydroxymethyl, ethyl, —CF$_3$, —CHF$_2$, or halogen, and which may optionally be mono- or polysubstituted by one or more groups selected from the group consisting of C$_1$–C$_4$-alkyl, hydroxy, halogen, —CF$_3$, and —OC$_1$–C$_4$-alkyl, or R$^3$ and R$^4$ together with the nitrogen atom form a 5- or 6-membered saturated or unsaturated heterocyclic ring which may optionally contain one or two more heteroatoms selected from the group consisting of nitrogen, oxygen, or sulfur, and which may optionally be mono- or polysubstituted by one or more groups selected from the group consisting of C$_1$–C$_4$-alkyl hydroxy, halogen, —CF$_3$, phenyl, benzyl, and —OC$_1$–C$_4$-alkyl, or R$^3$ and R$^4$ together with the nitrogen atom form a 5- or 6-membered saturated or unsaturated heterocyclic ring which is substituted by a 5- or 6-membered heteroaryl ring, which may optionally be mono- or polysubstituted by methyl, halogen, hydroxy, —CF$_3$, or methoxy, optionally in the form of the individual enantiomers or diastereomers, mixtures of the enantiomers or diastereomers and optionally in the form of the racemates, and optionally in the form of the acid addition salts, solvates and hydrates thereof, with the proviso that if A denotes

R$^1$ denotes methyl, and R$^3$ denotes hydrogen, R$^4$ cannot denote phenyl, pentafluorophenyl, 2-chloro-4-trifluoromethylphenyl, 3-chloro-4-methoxyphenyl, or cyclopentyl; and with the proviso that if A denotes

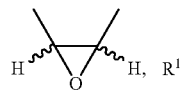

R$^1$ denotes methyl and R$^3$ denotes hydrogen, R$^4$ cannot denote phenyl.

Preferred are intermediates of general formula 4 wherein:
A denotes a double-bonded group selected from among:

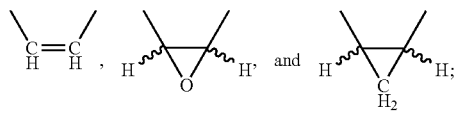

$R^1$ denotes $C_1$–$C_3$-alkyl, which may optionally be substituted by a group selected from the group consisting of $C_3$–$C_5$-cycloalkyl, hydroxy, or fluorine, or $R^1$ denotes $C_3$–$C_4$-alkylene-X, wherein X may represent chloride, bromide, methanesulfonate, or p-toluenesulfonate;

$R^3$ and $R^4$, which may be identical or different, denote
  (a) hydrogen, or
  (b) $C_1$–$C_5$-alkyl, which may optionally be substituted by a group selected from the group consisting of hydroxy, fluorine, —$CF_3$, and methoxy, or
  (c) a phenyl or naphthyl group which may optionally be substituted by one, two, or three groups selected from the group consisting of methyl, ethyl, hydroxy, fluorine, chlorine, bromine, —$CF_3$, methoxy, phenyl, and phenyl which may be mono-, di- or trisubstituted by methyl, fluorine, chlorine, bromine, hydroxy, —$CF_3$, or methoxy, or
  (d) a phenyl or naphthyl group which is substituted by a heteroaryl ring selected from the group consisting of furan, thiophene, pyrrole, imidazole, pyridine,. and pyrimidine, which may optionally be mono- or disubstituted by methyl, fluorine, chlorine bromine, hydroxy, —$CF_3$, or methoxy, or
  (e) a benzyl or phenylethyl group which may optionally be substituted at the phenyl ring by one, two, or three groups selected from the group consisting of methyl, ethyl, hydroxy, fluorine, chlorine, bromine, —$CF_3$, methoxy, phenyl, and phenyl which may be mono-, di-, or trisubstituted by methyl, fluorine, chlorine, bromine, hydroxy, —$CF_3$, or methoxy, or
  (f) a benzyl or phenylethyl group which is substituted at the phenyl ring by a heteroaryl ring selected from the group consisting of furan, thiophene, pyrrole, imidazole, pyridine, and pyrimidine, which may optionally be mono- or disubstituted by methyl, fluorine, chlorine bromine, hydroxy, —$CF_3$, or methoxy, or
  (g) a benzyl or phenylethyl group which may optionally be substituted at the alkylene bridge by one or two, preferably one group selected from the group consisting of methyl, ethyl, hydroxy, fluorine, chlorine, bromine, —$CF_3$, methoxy, and phenyl, or
  (h) a 5- or 6-membered saturated or unsaturated ring which may contain one, two or three heteroatoms selected from the group consisting of nitrogen, oxygen, or sulfur, and which may optionally be mono-, di-, or trisubstituted by one or more groups selected from the group consisting of methyl, ethyl, hydroxy, fluorine, chlorine, bromine, —$CF_3$, phenyl, benzyl, and methoxy, or
  (i) a 5- or 6-membered saturated or unsaturated ring which may contain one, two, or three heteroatoms selected from the group consisting of nitrogen, oxygen, or sulfur, and which is substituted by a heteroaryl ring selected from the group consisting of furan, thiophene, pyrrole, imidazole, pyridine, and pyrimidine, which may optionally be mono- or disubstituted by methyl, fluorine, chlorine, bromine, hydroxy, —$CF_3$, or methoxy, or
  (j) a cyclopentyl or cyclohexyl group which may optionally be substituted by one, two or three groups selected from the group consisting of methyl, ethyl, hydroxy, fluorine, chlorine, bromine, —$CF_3$, methoxy, phenyl, and phenyl which may be mono-, di-, or trisubstituted by methyl, fluorine, chlorine, bromine, hydroxy, —$CF_3$, or methoxy, or
  (k) a cyclopentyl or cyclohexyl group which is substituted by a heteroaryl ring selected from the group consisting of furan, thiophene, pyrrole, imidazole, pyridine, and pyrimidine, which may optionally be mono- or disubstituted by methyl, fluorine, chlorine bromine, hydroxy, —$CF_3$, or methoxy, or
  (l) a group of formula

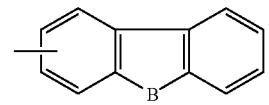

wherein B denotes —$CH_2$—, —NH—, —S—, or —O—, which may optionally be mono-, di- or trisubstituted by one or more groups selected from the group consisting of methyl, fluorine, chlorine, bromine, hydroxy, —$CF_3$, or methoxy, or
  (m) a group of formula

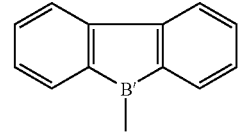

wherein B' denotes CH or N, which may optionally be mono-, di- or trisubstituted by one or more groups selected from the group consisting of methyl, fluorine, chlorine, bromine, hydroxy, —$CF_3$, or methoxy, or
  (n) a group of formula

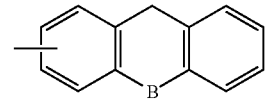

wherein B denotes —$CH_2$—, —NH—, —S—, or —O—, which may optionally be mono-, di-, or trisubstituted by one or more groups selected from the group consisting of methyl, fluorine, chlorine, bromine, hydroxy, —$CF_3$, or methoxy, or
  (o) a group of formula

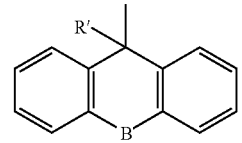

wherein B denotes —$CH_2$—, —NH—, —S—, or —O—, and
  R' may represent hydrogen, hydroxy, methyl, hydroxymethyl, ethyl, —$CF_3$, —$CHF_2$, or fluorine, and which may optionally be mono-, di-, or trisubstituted by one or more groups selected from the group consisting of methyl, fluorine, chlorine, bromine, hydroxy, —CF$_3$, or methoxy, or $R^3$ and $R^4$ together with the nitrogen atom form a 5- or 6-membered saturated or unsaturated heterocyclic ring which may optionally contain one or two more heteroatoms selected from the group consisting of nitrogen, oxygen, or sulfur, and which may optionally be mono-, di-, or trisubstituted by one or more groups selected from the group consisting of methyl, fluorine, chlorine, bromine, hydroxy, phenyl, —CF$_3$, or methoxy, or $R^3$ and $R^4$ together with the nitrogen atom form a 5- or 6-membered saturated or unsaturated heterocyclic ring which may optionally contain one or two more heteroatoms selected from the group consisting of nitrogen, oxygen or sulfur, which is substituted by a heteroaryl ring selected from the group consisting of furan, thiophene, pyrrole, imidazole, pyridine, and pyrimidine, which may optionally be mono- or disubstituted by methyl, fluorine, chlorine, bromine, hydroxy, —CF$_3$, or methoxy, optionally in the form of the individual enantiomers or diastereomers, mixtures of the enantiomers or diastereomers and optionally in the form of the racemates, and optionally in the form of the acid addition salts, solvates and hydrates thereof, with the proviso that if A denotes

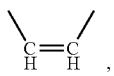

denotes methyl, and $R^3$ denotes hydrogen, $R^4$ cannot represent phenyl, 2-chloro-4-trifluoromethylphenyl, 3-chloro-4-methoxyphenyl, or cyclopentyl; and with the proviso that if A denotes

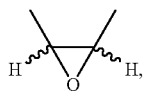

$R^1$ denotes methyl, and $R^3$ denotes hydrogen, $R^4$ cannot represent phenyl.

Particularly preferred are intermediates of general formula 4 wherein:

A denotes a double-bonded group selected from among:

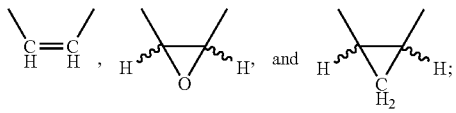

$R^1$ denotes a methyl or ethyl group which may optionally be substituted by cyclopropyl, hydroxy, or fluorine, or $R^1$ denotes $C_3$–$C_4$-alkylene-X, wherein X may represent chloride, bromide, methanesulfonate, or p-toluenesulfonate;

$R^3$ denotes hydrogen or $C_1$–$C_3$-alkyl, which may optionally be substituted by a group selected from the group consisting of hydroxy, fluorine, or —CF$_3$;

$R^4$ denotes $C_1$–$C_3$-alkyl, which may optionally be substituted by a group selected from the group consisting of hydroxy, fluorine, or —CF$_3$, or $R^4$ denotes a phenyl group which may optionally be substituted by one or two, preferably one group selected from the group consisting of furyl, thienyl, phenyl, and phenyl which may be mono-, di-, or trisubstituted by methyl, fluorine, chlorine, bromine, hydroxy, —CF$_3$, or methoxy, or $R^4$ denotes a benzyl group which may optionally be substituted at the phenyl ring by one, two, or three, preferably one group selected from the group consisting of methyl, ethyl, hydroxy, fluorine, chlorine, bromine, —CF$_3$, methoxy, furyl, thienyl, and phenyl, or $R^4$ denotes a benzyl group which may optionally be substituted at the methylene bridge by one, two, or three, preferably one group selected from the group consisting of methyl, ethyl, hydroxy, fluorine, chlorine, bromine, —CF$_3$, methoxy, and phenyl, or $R^4$ denotes a group of formula

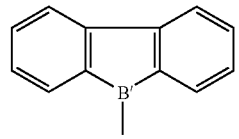

wherein B' denotes CH, which may optionally be mono- or disubstituted by one or more groups selected from the group consisting of methyl, fluorine, chlorine, bromine, hydroxy, —CF$_3$, or methoxy, optionally in the form of the individual enantiomers or diastereomers, mixtures of the enantiomers or diastereomers and optionally in the form of the racemates, and optionally in the form of the acid addition salts, solvates and hydrates thereof, with the proviso that if A denotes

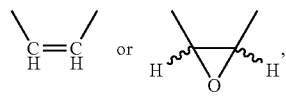

$R^1$ denotes methyl, and $R^3$ denotes hydrogen, $R^4$ cannot represent phenyl.

Also of particular interest are intermediates of general formula 4, wherein:

A denotes a double-bonded group selected from among:

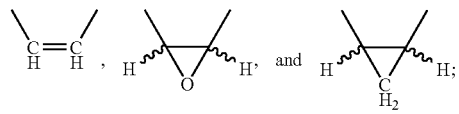

$R^1$ denotes a methyl or ethyl group which may optionally be substituted by cyclopropyl, hydroxy, or fluorine, or $R^1$ denotes $C_3$–$C_4$-alkylene-X, where X denotes chloride, bromide, methanesulfonate, and p-toluenesulfonate;

$R^3$ denotes hydrogen or $C_1$–$C_3$-alkyl; which may optionally be substituted by a group selected from the group consisting of hydroxy, fluorine, or —CF$_3$;

$R^4$ denotes $C_1$–$C_3$-alkyl, which may optionally be substituted by a group selected from the group consisting of hydroxy, fluorine, or —CF$_3$, or $R^4$ denotes a phenyl group which may optionally be substituted by phenyl, which may optionally be mono- or disubstituted by methyl, fluorine, hydroxy, or —CF$_3$, or $R^4$ denotes a benzyl group which may optionally be substituted at the phenyl ring by one or two, preferably one group, selected from the group consisting of methyl, ethyl, hydroxy, fluorine, —CF$_3$, and phenyl, or $R^4$ denotes a benzyl group which may optionally be mono-substituted by phenyl at the methylene bridge, or R$^4$ denotes a group of formula

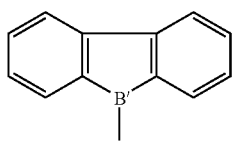

wherein B' denotes CH, which may optionally be mono- or disubstituted by one or more groups selected from the group consisting of methyl, fluorine, chlorine, bromine, hydroxy, —CF$_3$, or methoxy, optionally in the form of the individual enantiomers or diastereomers, mixtures of the enantiomers or diastereomers and optionally in the form of the racemates, and optionally in the form of the acid addition salts, solvates and hydrates thereof, with the proviso that if A denotes

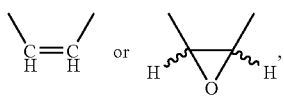

R$^1$ denotes methyl, and R$^3$ denotes hydrogen, R$^4$ cannot represent phenyl.

Of exceptional importance according to the invention are intermediates of general formula 4 wherein:

A denotes a double-bonded group selected from among:

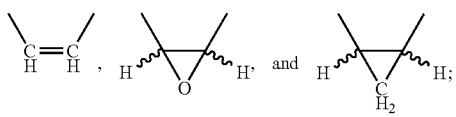

R$^1$ denotes methyl;

R$^3$ denotes hydrogen or methyl;

R$^4$ denotes biphenyl, benzhydryl, fluorenyl or biphenylmethyl, optionally in the form of the individual enantiomers or diastereomers, mixtures of the enantiomers or diastereomers and optionally in the form of the racemates, and optionally in the form of the acid addition salts, solvates, and hydrates thereof.

By acid addition salts are meant salts selected from the group consisting of the hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate, preferably hydrochloride, hydrobromide, hydrosulfate, hydrophosphate, hydrofumarate, and hydromethanesulfonate.

The present invention also relates to the use of the abovementioned intermediates of formula 4 for preparing the compounds of formula 1.

The examples of synthesis described below serve to illustrate the present invention still further. However, they are to be regarded as only examples of the procedure, as further illustration of the invention, without restricting the invention to the object described below by way of example.

EXAMPLE 1 tropenol biphen-2-ylcarbamate methobromide

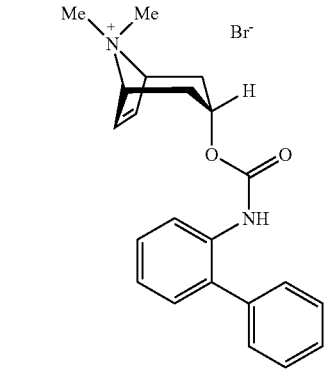

1.1.: tropenol biphen-2-ylcarbamate 5.0 g (0.026 mol) of 2-biphenylisocyanate is placed in 10 mL acetonitrile, and a solution of 3.619 g (0.026 mol) tropenol in 5 mL acetonitrile is added dropwise, then stirred for 24 hours at ambient temperature. The solution is concentrated by evaporation and the residue is distributed between dichloromethane and water. The organic phase is dried over sodium sulfate and evaporated to dryness. Yield: 7.4 g yellowish-orange oil (85% of theory).

1.2.: tropenol biphen-2-ylcarbamate methobromide 1.00 g (0.003 mol) of tropenol biphenyl-2-ylcarbamate and 1.709 g (0.009 mol) of 50% methyl bromide solution in acetonitrile are placed in 70 mL acetonitrile and left to stand for 3 days at ambient temperature in a sealed container and in the dark. The mixture is evaporated down to the residue. Purification is carried out by recrystallization first from ethanol-diethyl ether. Yield: 0.38 g white crystals (29% of theory); melting point: 244° C.–245° C.

EXAMPLE 2 scopine biphen-2-ylcarbamate methobromide

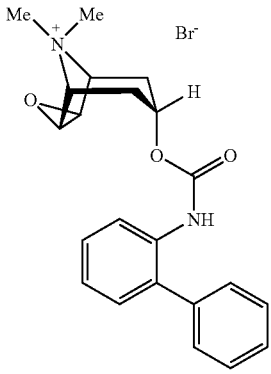

2.1.: scopine biphen-2-ylcarbamate hydrochloride 2.5 g (0.013 mol) of 2-biphenylisocyanate is placed in 7 mL acetonitrile, and a solution of 0.99 g (0.013 mol) scopine in 7 mL acetonitrile is added dropwise at ambient temperature. After 3 hours' reaction, the solution is concentrated by evaporation and the residue is distributed between dichloromethane and water. The organic phase is dried over sodium sulfate and evaporated to dryness. The residue is dissolved in dichloromethane, precipitated by the addition of ethereal HCl, then dissolved in water and washed with diethyl ether. The aqueous phase is made basic using 10% sodium carbonate solution and extracted with dichloromethane. Then the hydrochloride is precipitated. Yield: 1.57 g (31% of theory); melting point: 154° C.–155° C.

2.2.: scopine biphen-2-ylcarbamate methobromide

From 1.56 g (0.004 mol) of scopine biphen-2-ylcarbamate hydrochloride the free base is prepared by mixing with 10% sodium carbonate solution and subsequently extracting with methylene chloride. After drying over magnesium sulfate, the extract is evaporated to dryness, dissolved in 40 mL acetonitrile and 20 mL dichloromethane, combined with 3.5 g (0.012 mol) of approximately 50% methyl bromide solution in acetonitrile and left to stand 6 days at ambient temperature in a sealed container in the dark. The solution is evaporated to dryness. Purification is carried out by recrystallization from ethanol. Yield: 1.33 g (75% of theory); melting point: 216° C.–217° C.

EXAMPLE 3 tropenol biphen-2-ylmethylcarbamate methobromide

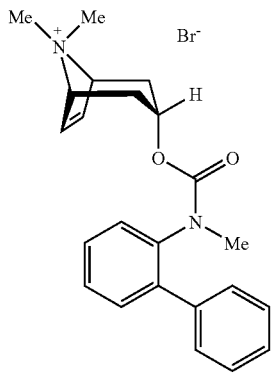

3.1.: scopine biphen-2-ylmethylcarbamate hydrochloride 2.5 g (0.007 mol) of tropenol biphenyl-2-ylcarbamate is dissolved at ambient temperature in 40 mL of tetrahydrofuran, combined with 0.45 g (0.011 mol) sodium hydride, and stirred for 0.5 hours at ambient temperature. Then 1.06 g (0.007 mol) of methyl iodide is added dropwise and the reaction mixture is stirred for 24 hours at ambient temperature. The suspension obtained is evaporated to dryness and distributed between dichloromethane and water. The organic phase is washed with water mixed with acetic acid (2 drops of glacial acetic acid to 100 mL of water), dried over magnesium sulfate, and evaporated to dryness. The residue is dissolved in dichloromethane, precipitated using ethereal HCl and recrystallized from isopropanol-diethyl ether. Yield: 0.23 g (9% of theory); melting point: 192° C.–194° C.

3.2.: scopine biphen-2-ylmethylcarbamate methobromide

From 0.2 g (0.001 mol) of scopine biphenyl-2-ylmethylcarbamate hydrochloride the free base is prepared by combining with 10% sodium carbonate solution and subsequently extracting with methylene chloride. The residue is dissolved in 50 mL acetonitrile and 30 mL dichloromethane and combined with 0.596 g (0.003 mol) of approximately 50% methyl bromide solution in acetonitrile. The solution is left to stand for 4 days in a sealed container in the dark at ambient temperature, then the solvent is distilled off under reduced pressure. Purification is carried out by recrystallization from acetonitrile. Yield: 0.06 g (14% of theory); melting point: 228° C.–229° C.

EXAMPLE 4 tropenol benzhydrylcarbamate methobromide

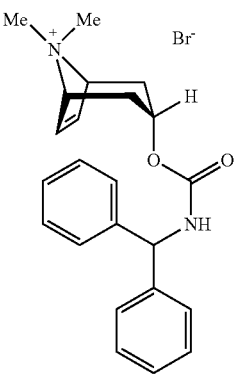

4.1.: tropenol benzhydrylcarbamate 2.5 g (0.012 mol) of diphenylmethylisocyanate is placed in 7 mL acetonitrile, a solution of 1.67 g (0.012 mol) of tropenol in 5 mL acetonitrile is added dropwise. The solution is stirred for 24 hours at ambient temperature; after 10 minutes, a white precipitate is formed. After the end of the reaction time, the suspension is cooled and the precipitate is suction filtered. Yield: 2.28 g (55% of theory); melting point: 140° C.–142° C.

4.2.: tropenol benzhydrylcarbamate methobromide 1.2 g (0.003 mol) of tropenol benzhydrylcarbamate is dissolved in 40 mL acetonitrile and 30 mL dichloromethane, 1.789 g (0.009 mol) of approximately 50% methyl bromide solution in acetonitrile are added and the mixture is left to stand for 4 days in a sealed container at ambient temperature. The solution is concentrated by evaporation and the residue recrystallized from acetonitrile. Yield: 0.76 g (57% of theory); melting point: 243° C.–244° C.

EXAMPLE 5 tropenol 9H-fluoren-9-ylcarbamate methobromide

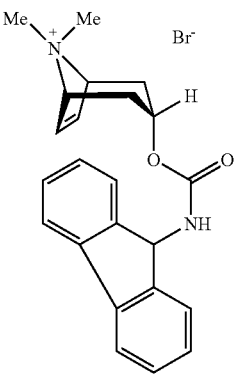

5.1.: tropenol 9H-fluoren-9-yl carbamate 1.95 g (0.009 mol) of 9-fluorene-9-isocyanate is suspended in 20 mL acetonitrile, a solution of 1.253 g (0.009 mol) of tropenol in 4 mL acetonitrile is added dropwise at ambient temperature, then stirred for 24 hours at this temperature. The reaction mixture is concentrated by evaporation in vacuo and distributed between dichloromethane and water. The organic phase is dried over magnesium sulfate and evaporated to dryness. The residue is dissolved in dichloromethane, precipitated by the addition of ethereal HCl, then dissolved in water and washed with diethyl ether.

The solid obtained is dissolved in water, combined with 10% sodium carbonate solution, extracted with dichloromethane, dried over magnesium sulfate, evaporated to dryness and recrystallized from acetonitrile. Yield: 0.32 g (10% of theory); melting point: 143° C.–144° C.

5.2.: tropenol 9H-fluoren-9-ylcarbamate methobromide 0.32 g (0.001 mol) of tropenol 9H-fluoren-9-ylcarbamate is dissolved in 30 mL acetonitrile and 50 mL dichloromethane, and 0.596 g (0.003 mol) of approximately 50% methyl bromide solution in acetonitrile are added. The solution is left to stand in a sealed container for 4 days at ambient temperature, then evaporated down to the residue and recrystallized from acetonitrile. Yield: 0.16 g (36% of theory); melting point: 226° C.–227° C.

EXAMPLE 6

Tropenol Biphen-2-ylmethylcarbamate methobromide

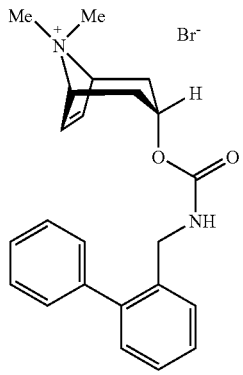

6.1.: tropenol biphen-2-ylmethylcarbamate 3.67 g (0.02 mol) of 2-phenylbenzylamine is placed in 250 mL saturated sodium bicarbonate solution and 250 mL dichloromethane. At 0° C., 52.9 mL (0.10 mol) of 20% phosgene-toluene solution are added under the surface of the dichloromethane. The mixture is vigorously stirred for 30 minutes. The two phases are separated, the organic phase is dried over sodium sulfate and evaporated to dryness. The residue is dissolved in 20 mL acetonitrile and 4.18 g (0.03 mol) of tropenol in 10 mL acetonitrile is added dropwise, whereupon a precipitate is formed. It is stirred for 12 hours at ambient temperature. The precipitate is suction filtered and the mother liquor evaporated to dryness. The residue is dissolved in dichloromethane and washed with water, water mixed with acetic acid (2 drops of glacial acetic acid to 100 mL of water), and 10% sodium carbonate solution. The organic phase is dried and evaporated to dryness. Yield: 2.85 g (41% of theory).

6.2.: tropenol biphen-2-ylmethylcarbamate methobromide 2.8 g (0.008 mol) of tropenol biphenyl-2-ylmethylcarbamate is dissolved in 10 mL acetonitrile and combined with 2.27 g (0.024 mol) 50% methyl bromide solution. The solution is left to stand for 4 days in a sealed container in the dark at ambient temperature. The solvent is concentrated by evaporation and the foamy residue is triturated with acetone until crystallization is complete. Yield: 2.78 g (78% of theory); melting point: 180° C.–181° C. (decomp.).

EXAMPLE 7

Scopine biphen-2-ylmethylcarbamate methobromide

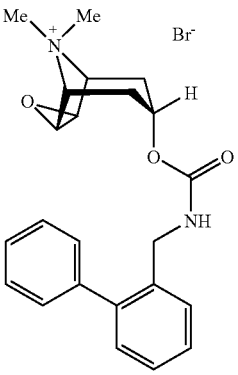

7.1.: scopine biphenyl-2-ylmethylcarbamate 3.67 g (0.02 mol) of 2-phenylbenzylamine is placed in 250 mL saturated sodium bicarbonate solution and 250 mL dichloromethane. At 0° C., 52.9 mL (0.10 mol) of 20% phosgene-toluene solution is added under the surface of the dichloromethane. It is stirred vigorously for 30 minutes. The two phases are separated, the organic phase is dried over sodium sulfate and evaporated to dryness. The residue is dissolved in 20 mL acetonitrile and 4.66 g (0.03 mol) of scopine in 10 mL acetonitrile are added dropwise, whereupon a precipitate is formed. It is stirred for 12 hours at ambient temperature. The precipitate is suction filtered and the mother liquor evaporated to dryness. The residue is dissolved in dichloromethane, washed with water, and then extracted with dilute hydrochloric acid (approximately 0.05 mol/L). The acidic aqueous phase is made basic with sodium carbonate and extracted with dichloromethane. The resulting organic phase is dried over sodium sulfate and evaporated to dryness. Yield: 2.85 g (33% of theory)

7.2.: scopine biphenyl-2-ylmethylcarbamate methobromide 1.2 g (0.003 mol) of scopine biphenyl-2-ylmethylcarbamate is dissolved in 5 mL acetonitrile and combined with 1.709 g (0.009 mol) of 50% methyl bromide solution. The solution is left to stand for 4 days in a sealed container in the dark at ambient temperature. The solvent is concentrated by evaporation and the foamy residue is triturated with acetone until crystallization is complete. Yield: 1.04 g (76% of theory); melting point: 175° C.–176° C.

EXAMPLE 8

9-methyl-9-azatricyclo[3.3.1.0*2.4*]non-7-yl biphen-2-ylcarbamate methobromide

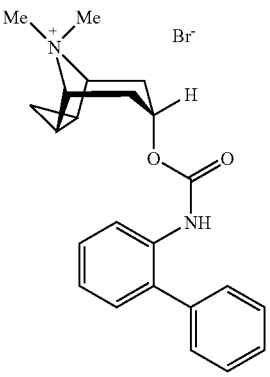

8.1.: 9-methyl-9-azatricyclo[3.3.1.0*2.4*]nonan-7-ol 35 mL (0.349 mol) of 40% aqueous KOH was covered with 100 mL diethyl ether and cooled in the ice bath, and 23.64 g (0.101 mol) of N-methyl-N-nitrosourea was added batchwise, then the mixture was stirred for 10 minutes. Then the ether phase was decanted off, again combined with diethyl ether, swirled around, and decanted off. The combined organic phases were dried over solid KOH while cooling with an ice bath and the solution obtained was further used. 25 mL of the diazomethane solution prepared above and then 53.4 mg (0.000139 mol) of bis(benzonitrile) dichloropalladium(II) was added to a solution of 4.01 g (0.028 mol) of tropenol in 25 mL diethyl ether and 5 mL of methanol while cooling with an ice bath. A further 8 mL of the diazomethane solution was added, then two lots of 10 mL of diazomethane solution, each after 30 minutes, and the mixture was then stirred for another 30 minutes. The solvent was concentrated by evaporation, extracted with hot hexane, filtered hot, evaporated to dryness. Yield: 4.25 g of slightly yellowish crystals (96% of theory).

8.2.: 9-methyl-9-azatricyclo[3.3.1.0*2.4*]non-7-yl Biphen-2-ylcarbamate hydrochloride 2.15 g of 9-methyl-9-azatricyclo[3.3.1.0*2.4*]nonan-7-ol in acetonitrile was added dropwise to a solution of 2.5 g of biphenyl-2-isocyanate in acetonitrile. The solution was stirred overnight at ambient temperature, diluted with 200 mL dichloromethane, and washed with water and water mixed with acetic acid (2 drops of glacial acetic acid to 100 mL of water). The organic phase was dried over magnesium sulfate, filtered, and concentrated by rotary evaporation. The yellow oil obtained was dissolved in dichloromethane, converted into the hydrochloride by the addition of ethereal HCl and recrystallized from acetonitrile/ether. Yield: 0.35 g of white crystals (7% of theory).

8.3.: 9-methyl-9-azatricyclo[3.3.1.0*2.4*]non-7-yl biphenyl-2-ylcarbamate methobromide 0.35 g of 9-methyl-9-azatricyclo[3.3.1.0*2.4*]non-7-yl biphenyl-2-ylcarbamate hydrochloride was dissolved in water, made basic with 10% sodium carbonate solution, and extracted with dichloromethane. The organic phase was dried over magnesium sulfate, filtered, and evaporated to dryness. The residue was dissolved in 10 mL acetonitrile, and after the addition of 1.2 g of 50% methyl bromide solution in acetonitrile, stirred for 30 days at 75° C. in a sealed pressure vessel. The solution was evaporated to dryness and the residue was recrystallized from acetonitrile. Yield: 0.16 g of white crystals (39% of theory); melting point: 142° C.–144° C.

It was found that the compounds of formula 1 according to the invention are antagonists of the M3 receptor (Muscarinic Receptor subtype 3). The compounds according to the invention have $K_i$ values of less than 1000 nM in terms of their affinity for the M3 receptor. These values were determined by the method described below.

Chemicals $^3$H-NMS was obtained from Messrs Amersham of Braunschweig, with a specific radioactivity of 3071 GBq/mmol (83 Ci/mmol). All the other reagents were obtained from Serva of Heidelberg and Merck of Darmstadt.

Cell Membranes

We used cell membranes from CHO (Chinese hamster ovary) cells which were transfected with the corresponding genes of the human muscarinic receptor subtypes hm1 to hm5 (BONNER). The cell membranes of the desired subtype were thawed, resuspended by hand with a glass homogenizer and diluted with HEPES buffer to a final concentration of 2–30 mg of protein/mL.

Receptor Binding Studies

The binding assay was carried out in a final volume of 200 μL and consisted of 50 μL of unlabelled substance in various concentrations, 50 μL of radioligand (3H—N-methylscopolamine 2 nmol/L (3H-NMS)), and 100 μL of membrane preparation in TRIS buffer (50 mmol/L TRIS, 10 mmol/L $MgCl_2$, 100 mmol/L NaCl, adjusted with 1 mol/L NaOH to pH 7.4).

The non-specific binding was determined by displacement with 10 μmol/L of atropine. The preparation was incubated for 1 hour at ambient temperature in 96-well microtitre plates (Beckman, polystyrene, No. 267001) as a double measurement. The incubation was ended by filtering using a Skatron Cell Harvester (type IH 110) through Whatman GF/C filters. The filters were washed with 3 mL of ice-cooled TRIS buffer. The filters were then transferred into scintillation vials (Zinsser 5 mL), 4 mL of scintillation liquid were added (Zinsser: Quickszint 2000 or Beckmann Ultima Gold) and the vials were shaken end over end for 1 hour.

Determining the Radioactivity

The radioactivity of the filters was measured using a scintillation counter (Beckmann or LKB).

Evaluation

The $K_i$ values were calculated using implicit equations which were derived directly from the mass-action law, with the model for the 1 receptor 2 ligand reaction (SysFit software, SCHITTKOWSKI).

Literature

BONNER TI, New Subtypes of Muscarinic Acetylcholine Receptors, Trends Pharmacol. Sci. 10, Suppl.: 11–15 (1989); SCHITTKOWSKI K, Parameter Estimation in Systems of Nonlinear Equations, Numer Math. 68: 129–142 (1994).

The compounds of formula 1 according to the invention are characterized by their range of uses in the therapeutic field.

Particular mention should be made of those applications for which the compounds of formula 1 according to the invention may preferably be used on the basis of their pharmaceutical activity as anticholinergics. These are, for example, the treatment of asthma or chronic obstructive pulmonary disease (COPD). The compounds of general formula 1 may also be used to treat vagally induced sinus bradycardia and to treat heart rhythm disorders. Generally, the compounds according to the invention may also be used therapeutically to treat spasms, for example, in the gastrointestinal tract. They may also be used to treat spasms in the urinary tract and also to treat menstrual pain, for example. Of the ranges of indications mentioned above, the treatment of asthma and COPD with the compounds of formula 1 according to the invention is of particular importance.

The compounds of general formula 1 may be used on their own or in conjunction with other active substances of formula 1. The compounds of general formula 1 may optionally also be used in combination with other pharmacologically active substances. These may be, in particular, betamimetics, antiallergics, PAF antagonists, PDE-IV inhibitors, leukotriene antagonists, p38 kinase inhibitors, EGFR kinase inhibitors, and corticosteroids as well as combinations of active substances thereof.

Examples of betamimetics which may be used according to the invention in conjunction with the compounds of formula 1 include compounds selected from among bambuterol, bitolterol, carbuterol, clenbuterol, fenoterol, formoterol, hexoprenaline, ibuterol, pirbuterol, procaterol, reproterol, salmeterol, sulfonterol, terbutaline, tolubuterol, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol; 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert-butylamino)ethanol, and 1-(4-ethoxycarbonylamino-3-cyano-5-fluorophenyl)-2-(tert-butylamino)ethanol, optionally in the form of the racemates, the enantiomers, the diastereomers and optionally the pharmacologically acceptable acid addition salts, the solvates, and/or the hydrates thereof. Most preferably, the betamimetics used as active substances in conjunction with the compounds of formula 1 according to the invention are selected from among fenoterol, formoterol, salmeterol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, the enantiomers, the diastereomers and optionally the pharmacologically acceptable acid addition salts, and the hydrates thereof. Of the betamimetics mentioned above, the compounds formoterol and salmeterol are particularly preferred, optionally in the form of the racemates, the enantiomers, the diastereomers and optionally the pharmacologically acceptable acid addition salts thereof, and the hydrates thereof. According to the invention, the acid addition salts of the betamimetics selected, for example, from among the hydrochloride, hydrobromide, sulfate, phosphate, fumarate, methanesulfonate, and xinafoate are preferred. Particularly preferred in the case of salmeterol are the salts selected from among the hydrochloride, sulfate, and xinafoate, of which the xinafoate is particularly preferred. Particularly preferred in the case of formoterol are the salts selected from among the hydrochloride, sulfate, and fumarate, of which the hydrochloride and fumarate are particularly preferred. According to the invention, formoterol fumarate is of exceptional importance.

Within the scope of the present invention, the corticosteroids which may optionally be used in conjunction with the compounds of formula 1 may be compounds selected from among flunisolide, beclomethasone, triamcinolone, budesonide, fluticasone, mometasone, ciclesonide, rofleponide, GW 215864, KSR 592, ST-126, and dexamethasone. Preferably, within the scope of the present invention, the corticosteroids are selected from among flunisolide, beclomethasone, triamcinolone, budesonide, fluticasone, mometasone, ciclesonide, and dexamethasone, while budesonide, fluticasone, mometasone, and ciclesonide are important and budesonide and fluticasone are particularly important. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or furoates. In some cases, the corticosteroids may also occur in the form of their hydrates.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A, and AWD-12-281. Preferred PDE-IV inhibitors are selected from among enprofylline, roflumilast, ariflo, and AWD-12-281, while AWD-12-281 is particularly preferred as the combination partner with the compound of formula 1 according to the invention. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, according to the invention, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid. According to the invention, the salts selected from among the acetate, hydrochloride, hydrobromide, sulfate, phosphate, and methanesulfonate are preferred in this context.

Within the scope of the present invention, the term dopamine agonists, which may optionally be used in conjunction with the compounds of formula 1, denotes compounds selected from among bromocriptine, cabergoline, alpha-dihydroergocryptine, lisuride, pergolide, pramipexol, roxindole, ropinirole, talipexole, terguride, and viozan. It is preferable within the scope of the present invention to use, as combination partners with the compounds of formula 1, dopamine agonists selected from among pramipexol, talipexole and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of antiallergic agents which may be used according to the invention as a combination with the compound of formula 1 include epinastine, cetirizine, azelastine, fexofenadine, levocabastine, loratadine, mizolastine, ketotifene, emedastine, dimetindene, clemastine, bamipine, hexachloropheniramine, pheniramine, doxylamine, chlorophenoxamine, dimenhydrinate, diphenhydramine, promethazine, ebastine, desloratadine, and meclizine. Preferred antiallergic agents which may be used within the scope of the present invention in combination with the compounds of formula 1 according to the invention are selected from among epinastine, cetirizine, azelastine, fexofenadine, levocabastine, loratadine, ebastine, desloratadine, and mizolastine, epinastine, and desloratadine being particularly preferred. Any reference to the abovementioned antiallergic agents also includes, within the scope of the present invention, a reference to any pharmacologically acceptable acid addition salts thereof which may exist.

Examples of PAF antagonists which may be used according to the invention as a combination with the compounds of formula 1 include 4-(2-chlorophenyl)-9-methyl-2-[3-(4-morpholinyl)-3-propanon-1-yl]-6H-thieno[3,2-f][1,2,4]triazolo[4,3-α][1,4]diazepine and 6-(2-chlorophenyl)-8,9-dihydro-1-methyl-8-[(4-morpholinyl)carbonyl]-4H,7H-cyclopenta-[4,5]thieno[3,2-f][1,2,4]triazolo[4,3-α][1,4]diazepine.

Examples of EGFR kinase inhibitors which may be used as a combination with the compounds of formula 1 according to the invention include, in particular, 4-[(3-chloro-4-fluorophenyl)amino]-7-[4-((R)-6-methyl-2-oxomorpholin-4-yl)butyloxy]-6-[(vinylcarbonyl)amino]quinazoline, 4-[(3-chloro-4-fluorophenyl)amino]-7-[4-((S)-6-methyl-2-oxomorpholin-4-yl)butyloxy]-6-[(vinylcarbonyl)amino]quinazoline, 4-[(3-chloro-4-fluorophenyl)amino]-7-(2-{4-[(S)-(2-oxotetrahydrofuran-5-yl)carbonyl]piperazin-1-yl}ethoxy)-6-[(vinylcarbonyl)amino]quinazoline, 4-[(3-chloro-4-fluorophenyl)amino]-7-[2-((S)-6-methyl-2-oxomorpholin-4-yl)ethoxy]-6-[(vinylcarbonyl)amino]quinazoline, 4-[(3-chloro-4-fluorophenyl)amino]-6-[(4-{N-[2-(ethoxycarbonyl)ethyl]-N-[(ethoxycarbonyl)methyl]amino}-1-oxo-2-buten-1-yl)amino]-7-cyclopropylmethoxy-quinazoline, 4-[(R)-(1-phenylethyl)amino]-6-{[4-(morpholin-4-yl)-1-oxo-2-buten-1-yl]-amino}-7-cyclopropylmethoxyquinazoline, and 4-[(3-chloro-4-fluorophenyl)amino]-6-[3-(morpholin-4-yl)propyloxy]-7-methoxyquinazoline. Any reference to the abovementioned EGFR kinase inhibitors also includes, within the scope of the present invention, a reference to any pharmacologically acceptable acid addition salts thereof which may exist. By the physiologically or pharmacologically acceptable acid addition salts thereof which may be formed by the EGFR kinase inhibitors are meant, according to the invention, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid. The salts of the EGFR kinase inhibitors selected from among the salts of acetic acid, hydrochloric acid, hydrobromic acid, sulfuric acid, phosphoric acid, and methanesulfonic acid are preferred according to the invention.

Particularly preferred examples of p38 kinase inhibitors which may be used as a combination with the compounds of formula 1 according to the invention include 1-[5-tert-butyl-2-p-tolyl-2H-pyrazol-3-yl]-3-[4-(2-morpholin-4-ylethoxy)naphthalin-1-yl]urea, 1-[5-tert-butyl-2-p-tolyl-2H-pyrazol-3-yl]-3-[4-(2-(1-oxothiomorpholin-4-yl)ethoxy)naphthalin-4-yl)ethoxy)naphthalin-1-yl]urea, 1-[5-tert-butyl-2-(2-methylpyridin-5-yl)-2H-pyrazol-3-yl]-3-[4-(2-pyridin-4-ylethoxy)naphthalin-1-yl]urea, 1-[5-tert-butyl-2-(2-methoxypyridin-5-yl)-2H-pyrazol-3-yl]-3-[4-(2-morpholin-4-ylethoxy)naphthalin-1-yl]urea, and 1-[5-tert-butyl-2-methyl-2H-pyrazol-3-yl]-3-[4-(2-morpholin-4-ylethoxy)naphthalen-1-yl]urea. Any reference to the abovementioned p38 kinase inhibitors also includes, within the scope of the present invention, a reference to any pharmacologically acceptable acid addition salts thereof which may exist. By the physiologically or pharmacologically acceptable acid addition salts thereof which may be formed by the p38 kinase inhibitors are meant, according to the invention, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

If the compounds of formula 1 are used in conjunction with other active substances, the combination with steroids, PDE IV inhibitors or betamimetics is particularly preferred, of the categories of compounds mentioned above. The combination with betamimetics, particularly with long-acting betamimetics, is of particular importance. The combination of the compounds of formula 1 according to the invention with salmeterol or formoterol is particularly preferred.

Suitable preparations for administering the salts of formula 1 include for example tablets, capsules, suppositories and solutions, etc. Administration of the compounds according to the invention by inhalation is of particular importance according to the invention (particularly for treating asthma or COPD). The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the. tablets with substances normally used for tablet coatings, for example, collidone or shellac, gum arabic, talc, titanium dioxide, or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates or stabilizers such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may, for example, be prepared by mixing the active substances with inert carriers such as lactose or sorbitol and packing them into gelatine capsules.

Suitable suppositories may be made, for example, by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, and chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone), and lubricants (e.g., magnesium stearate, talc, stearic acid, and sodium lauryl sulfate).

For oral use, the tablets may obviously contain, in addition to the carriers specified, additives such as sodium citrate, calcium carbonate, and dicalcium phosphate together with various additional substances such as starch, preferably potato starch, gelatin, and the like. Lubricants such as magnesium stearate, sodium lauryl sulfate, and talc may also be used to produce the tablets. In the case of aqueous suspensions, the active substances may be combined with various flavor enhancers or colorings in addition to the above-mentioned excipients.

For administering the compounds of formula 1 for the treatment of asthma or COPD, it is particularly preferred according to the invention to use preparations or pharmaceutical formulations which are suitable for inhalation. Inhalable preparations include inhalable powders, propellant-containing metering aerosols, or propellant-free inhalable solutions Within the scope of the present invention, the term propellant-free inhalable solutions also includes concentrates or sterile inhalable solutions ready for use. The formulations which may be used within the scope of the present invention are described in more detail in the next part of the specification The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, or maltose), oligo- and polysaccharides (e.g., dextrans), polyalcohols (e.g., sorbitol, mannitol, or xylitol), salts (e.g., sodium chloride or calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 µm and 150 µm, most preferably between 15 µm and 80 µm. It may sometimes seem appropriate to add finer excipient fractions with an average particle size of 1 µm to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 µm to 10 µm, more preferably from 1 µm to 5 µm, is added to the excipient mixture. Processes for producing the inhalable powders according to the invention by grinding and micronizing and finally mixing the ingredients together are known from the prior art. The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane, or isobutane and halohydrocarbons such as fluorinated derivatives of methane, ethane, propane, butane, cyclopropane, or cyclobutane. The abovementioned propellant gases may be used either on their own or in mixtures thereof. Particularly preferred propellant gases are halogenated alkane derivatives selected from TG134a and TG227 and mixtures thereof.

The propellant-driven inhalation aerosols may also contain other ingredients such as cosolvents, stabilizers, surfactants, antioxidants, lubricants, and pH adjusters. All these ingredients are known in the art.

The propellant-driven inhalation aerosols according to the invention mentioned above may be administered using inhalers known in the art, such as metered dose inhalers (MDIs).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid etc. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may be used, particularly in the case of acids which have other properties in addition to their acidifying qualities, e.g., as flavorings, antioxidants or complexing agents, such as citric acid or ascorbic acid, for example. According to the invention, it is particularly preferred to use hydrochloric acid to adjust the pH.

The addition of edetic acid (EDTA) or one of the known salts thereof, sodium edetate, as stabilizer or complexing agent may optionally be omitted in these formulations. Other embodiments may contain this compound or these compounds. In a preferred embodiment, the content based on sodium edetate is less than 100 mg/100 mL, preferably less than 50 mg/100 mL, more preferably less than 20 mg/100 mL. Generally, inhalable solutions in which the content of sodium edetate is from 0 to 10 mg/100 mL are preferred.

Cosolvents and/or other excipients may be added to the propellant-free inhalable solutions according to the invention. Preferred cosolvents are those which contain hydroxyl groups or other polar groups, e.g., alcohols, particularly isopropyl alcohol, glycols, particularly propyleneglycol, polyethyleneglycol, polypropyleneglycol, glycol ether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants, and/or preservatives which guarantee or prolong the shelf life of the finished pharmaceutical formulation, flavorings, vitamins, and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art. The preservatives mentioned above are preferably present in concentrations of up to 50 mg/100 mL, more preferably between 5 and 20 mg/100 mL.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterized by a high potency even at doses in the µg range. The compounds of formula 1 may also be used effectively above the µg range. The dosage may then be in the gram range, for example.

Particularly when administered by routes other than by inhalation, the compounds according to the invention may be administered in higher doses (for example, but not restrictively, in the range from 1 to 1000 mg).

The following examples of formulations illustrate the present invention without restricting its scope.

| A. Tablets | per tablet |
| --- | --- |
| active substance 1 | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated, and dried. The granules, the remaining corn starch and the magnesium stearate are screened and mixed together. The mixture is compressed to produce tablets of suitable shape and size.

| B. Tablets | per tablet |
| --- | --- |
| active substance 1 | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C. Ampoule Solution | |
| --- | --- |
| active substance 1 | 50 mg |
| sodium chloride | 50 mg |
| water for inj. | 5 mL |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg, and 50 mg of active substance.

| D. Metering Aerosol | |
| --- | --- |
| active substance 1 | 0.005 |
| sorbitan trioleate | 0.1 |
| monofluorotrichloromethane and difluorodichloromethane (2:3) | to 100 |

The suspension is transferred into a conventional aerosol container with metering valve. Preferably 50 µL suspension are released on each actuation. The active substance may also be released in higher doses if desired (e.g., 0.02 wt.-%).

| E) Solutions (in mg/100 mL) | |
| --- | --- |
| active substance 1 | 333.3 mg |
| formoterol fumarate | 333.3 mg |
| benzalkonium chloride | 10.0 mg |
| EDTA | 50.0 mg |
| HCl (1N) | to pH 3.4 |

This solution may be prepared in the usual way.

| F. Inhalable Powder | |
|---|---|
| active substance 1 | 8 μg |
| formoterol fumarate | 6 μg |
| lactose monohydrate | to 25 mg |

The inhalable powder is prepared in the usual way by mixing the individual ingredients.

| G. Inhalable Powder | |
|---|---|
| active substance 1 | 9 μg |
| lactose monohydrate | to 5 mg |

The inhalable powder is prepared in the usual way by mixing the individual ingredients.

We claim:

1. A compound of formula 1

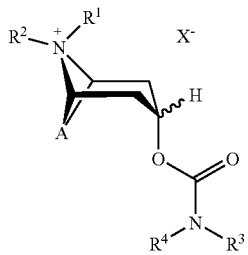

wherein:

A is 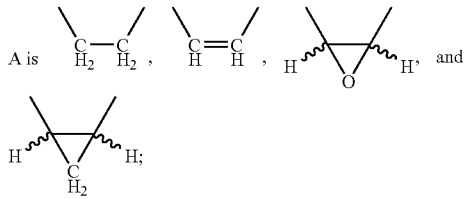

and;

$X^-$ is an anion with a single negative charge;

$R^1$ and $R^2$, which are identical or different, are each $C_1$–$C_5$-alkyl optionally substituted by a $C_3$–$C_6$-cycloalkyl, hydroxy, or halogen, or $R^1$ and $R^2$ together are a $C_3$–$C_5$-alkylene bridge; and $R^3$ and $R^4$, which are identical or different, are each:
  (a) hydrogen, or
  (b) $C_1$–$C_5$-alkyl optionally mono- or polysubstituted by hydroxy, halogen, —$CF_3$, or —$OC_1$–$C_4$-alkyl, or
  (c) a $C_2$–$C_5$-alkenyl or $C_2$–$C_5$-alkynyl group, each optionally mono- or polysubstituted by hydroxy, halogen, —$CF_3$, —$OC_1$–$C_4$-alkyl, phenyl, or phenyl mono- or polysubstituted by methyl, halogen, hydroxy, —$CF_3$, or methoxy, or
  (d) $C_6$–$C_{10}$-aryl optionally substituted by one or more groups selected from $C_1$–$C_4$-alkyl, hydroxy, fluorine, bromine, —$CF_3$, —$OC_1$–$C_4$-alkyl, phenyl, or phenyl mono- or polysubstituted by methyl, fluorine, bromine, hydroxy, —$CF_3$, or methoxy, or
  (e) $C_6$–$C_{10}$-aryl substituted by a 5- or 6-membered heteroaryl ring optionally mono- or polysubstituted by methyl, halogen, hydroxy, —$CF_3$, or methoxy, or
  (f) $C_6$–$C_{10}$-aryl-$C_1$–$C_4$-alkylene optionally substituted at the aryl group by one or more groups selected from $C_1$–$C_4$-alkyl, hydroxy, halogen, —$CF_3$, —$OC_1$–$C_4$-alkyl, phenyl, or phenyl mono- or polysubstituted by methyl, halogen, hydroxy, —$CF_3$, or methoxy, or
  (g) $C_6$–$C_{10}$-aryl-$C_1$–$C_4$-alkylene substituted at the aryl group by a 5- or 6-membered heteroaryl ring optionally mono- or polysubstituted by methyl, halogen, hydroxy, —$CF_3$, or methoxy, or
  (h) $C_6$–$C_{10}$-aryl-$C_1$–$C_4$-alkylene optionally substituted at the alkylene group by one or more groups selected from $C_1$–$C_4$-alkyl, hydroxy, halogen, —$CF_3$, —$OC_1$–$C_4$-alkyl, or phenyl, or
  (i) a 5- or 6-membered saturated or unsaturated ring having one, two, or three heteroatoms selected from nitrogen, oxygen, or sulfur, and which is optionally mono- or polysubstituted by one or more groups selected from $C_1$–$C_4$-alkyl hydroxy, halogen, —$CF_3$, phenyl, benzyl, or —$OC_1$–$C_4$-alkyl, or
  (j) a 5- or 6-membered saturated or unsaturated ring having contain one, two, or three heteroatoms selected from nitrogen, oxygen, or sulfur and which is substituted by a 5- or 6-membered heteroaryl ring, which is optionally mono- or polysubstituted by methyl, halogen, hydroxy, —$CF_3$, or methoxy, or
  (k) $C_3$–$C_6$-cycloalkyl optionally substituted by one or more groups selected from $C_1$–$C_4$-alkyl, hydroxy, halogen, —$CF_3$, —$OC_1$–$C_4$-alkyl, phenyl, or phenyl mono- or polysubstituted by methyl, halogen, hydroxy, —$CF_3$, or methoxy, or
  (l) $C_3$–$C_6$-cycloalkyl substituted by a 5- or 6-membered heteroaryl ring optionally mono- or polysubstituted by methyl, halogen, hydroxy, —$CF_3$, or methoxy, or
  (m) a group of formula

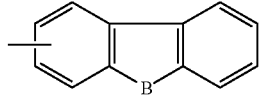

wherein B is —$CH_2$—, —NH—, —S—, or —O—, which is optionally mono- or polysubstituted by one or more groups selected from $C_1$–$C_4$-alkyl, hydroxy, halogen, —$CF_3$, or —$OC_1$–$C_4$-alkyl, or (n) a group of formula

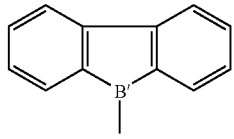

wherein B' is CH or N, which is optionally mono- or polysubstituted by one or more groups selected from $C_1$–$C_4$-alkyl, hydroxy, halogen, —$CF_3$, or —$OC_1$–$C_4$-alkyl, or (o) a group of formula

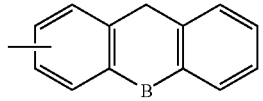

wherein B is —$CH_2$—, —NH—, —S—, or —O—, which is optionally mono- or polysubstituted by one or more groups selected from $C_1$–$C_4$-alkyl, hydroxy, halogen, —$CF_3$, and —$OC_1$–$C_4$-alkyl, or
(p) a group of formula

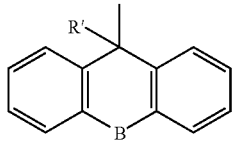

wherein B is —$CH_2$—, —NH—, —S—, or —O—, and

R' is hydrogen, hydroxy, methyl, hydroxymethyl, ethyl, —$CF_3$, —$CHF_2$, or halogen, and which is optionally mono- or polysubstituted by one or more groups selected from $C_1$–$C_4$-alkyl, hydroxy, halogen, —$CF_3$, or —$OC_1$–$C_4$-alkyl, or $R^3$ and $R^4$ together with the nitrogen atom form a 5- or 6-membered saturated or unsaturated heterocyclic ring having zero, one, or two more heteroatoms selected from nitrogen, oxygen, or sulfur, and which is optionally mono- or polysubstituted by one or more groups selected from $C_1$–$C_4$-alkyl hydroxy, halogen, —$CF_3$, phenyl, benzyl, or —$OC_1$–$C_4$-alkyl, or $R^3$ and $R^4$ together with the nitrogen atom form a 5- or 6-membered saturated or unsaturated heterocyclic ring substituted by a 5- or 6-membered heteroaryl ring optionally mono- or polysubstituted by methyl, halogen, hydroxy, —$CF_3$, or methoxy, or the pharmacologically acceptable acid addition salts, solvates, and hydrates thereof.

2. The compound of formula 1 according to claim 1, wherein $X^-$ is chloride, bromide, iodide, sulfate, phosphate, methanesulfonate, nitrate, maleate, acetate, citrate, fumarate, tartrate, oxalate, succinate, benzoate, or p-toluenesulfonate, or the pharmacologically acceptable acid addition salts, solvates, and hydrates thereof.

3. The compound of formula 1 according to claim 2, wherein $X^-$ is chloride, bromide, methanesulfonate, or p-toluenesulfonate, or the pharmacologically acceptable acid addition salts, solvates, and hydrates thereof.

4. The compound of formula 1 according to claim 3, wherein $X^-$ is bromide or methanesulfonate, or the pharmacologically acceptable acid addition salts, solvates, and hydrates thereof.

5. The compound of formula 1 according to one of claims 1, 2, 3, or 4, wherein:

A is

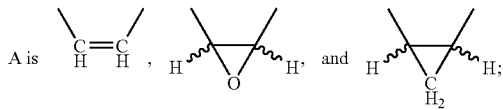

$R^1$ and $R^2$, which are identical or different, are each $C_1$–$C_3$-alkyl optionally substituted by a $C_3$–$C_5$-cycloalkyl, hydroxy, or fluorine, or $R^1$ and $R^2$ together are a $C_3$–$C_4$-alkylene bridge; and $R^3$ and $R^4$, which are identical or different, are each:
  (a) hydrogen, or
  (b) $C_1$–$C_5$-alkyl optionally substituted by hydroxy, fluorine, —$CF_3$, and methoxy, or
  (c) a phenyl or naphthyl group, each optionally substituted by one, two, or three groups selected from methyl, ethyl, hydroxy, fluorine, bromine, —$CF_3$, methoxy, phenyl, or phenyl mono-, di-, or trisubstituted by methyl, fluorine, bromine, hydroxy, —$CF_3$, or methoxy, or
  (d) a phenyl or naphthyl group, each optionally substituted by furan, thiophene, pyrrole, imidazole, pyridine, or pyrimidine, each optionally mono- or disubstituted by methyl, fluorine, chlorine, bromine, hydroxy, —$CF_3$, or methoxy, or
  (e) a benzyl or phenylethyl group, each optionally substituted at the phenyl ring by one, two, or three groups selected from methyl, ethyl, hydroxy, fluorine, chlorine, bromine, —$CF_3$, methoxy, phenyl, or phenyl mono-, di-, or trisubstituted by methyl, fluorine, chlorine, bromine, hydroxy, —$CF_3$, or methoxy, or
  (f) a benzyl or phenylethyl group, each substituted at the phenyl ring by furan, thiophene, pyrrole, imidazole, pyridine, or pyrimidine, which are optionally mono- or disubstituted by methyl, fluorine, chlorine, bromine, hydroxy, —$CF_3$, or methoxy, or
  (g) a benzyl or phenylethyl group, each optionally substituted at the alkylene bridge by one or two groups selected from methyl, ethyl, hydroxy, fluorine, chlorine, bromine, —$CF_3$, methoxy, or phenyl, or
  (h) a 5- or 6-membered saturated or unsaturated ring having one, two, or three heteroatoms selected from nitrogen, oxygen, or sulfur, and which is optionally mono-, di-, or trisubstituted by one or more groups selected from methyl, ethyl, hydroxy, fluorine, chlorine, bromine, —$CF_3$, phenyl, benzyl, or methoxy, or
  (i) a 5- or 6-membered saturated or unsaturated ring having one, two, or three heteroatoms selected from nitrogen, oxygen, or sulfur, and which is substituted by furan, thiophene, pyrrole, imidazole, pyridine, or pyrimidine, which is optionally mono- or disubstituted by methyl, fluorine, chlorine, bromine, hydroxy, —$CF_3$, or methoxy, or
  (j) a cyclopentyl or cyclohexyl group each optionally substituted by one, two, or three groups selected from methyl, ethyl, hydroxy, fluorine, chlorine, bromine, —$CF_3$, methoxy, phenyl, or phenyl mono-, di-, or trisubstituted by methyl, fluorine, chlorine, bromine, hydroxy, —$CF_3$, or methoxy, or
  (k) a cyclopentyl or cyclohexyl group each substituted by furan, thiophene, pyrrole, imidazole, pyridine, or pyrimidine, which is optionally mono- or disubstituted by methyl, fluorine, chlorine, bromine, hydroxy, —$CF_3$, or methoxy, or
  (l) a group of formula

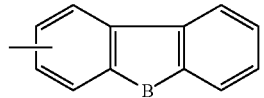

wherein B is —$CH_2$—, —NH—, —S—, or —O—, which is optionally mono-, di-, or trisubstituted by one or more groups selected from methyl, fluorine, chlorine, bromine, hydroxy, —$CF_3$ or methoxy, or (m) a group of formula

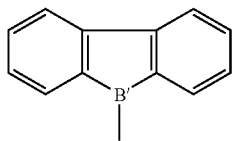

wherein B' is CH or N, which is optionally mono-, di-, or trisubstituted by one or more groups selected from methyl, fluorine, chlorine, bromine, hydroxy, —CF$_3$, or methoxy, or (n) a group of formula

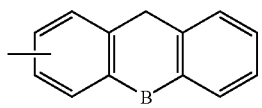

wherein B is —CH$_2$—, —NH—, —S—, or —O—, which is optionally mono-, di-, or trisubstituted by one or more groups selected from methyl, fluorine, chlorine, bromine, hydroxy, —CF$_3$, or methoxy, or (o) a group of formula

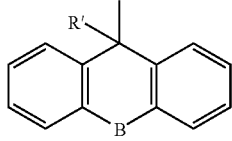

wherein B is —CH$_2$—, —NH—, —S—, or —O—, and

R' is hydrogen, hydroxy, methyl, hydroxymethyl, ethyl, —CF$_3$, —CHF$_2$, or fluorine, and which is optionally mono-, di-, or trisubstituted by one or more groups selected from methyl, fluorine, chlorine, bromine, hydroxy, —CF$_3$, or methoxy, or R$^3$ and R$^4$ together with the nitrogen atom form a 5- or 6-membered saturated or unsaturated heterocyclic ring having zero, one, or two more heteroatoms selected from nitrogen, oxygen, or sulfur, and which is optionally mono-, di-, or trisubstituted by one or more groups selected from methyl, fluorine, chlorine, bromine, hydroxy, phenyl, —CF$_3$, or methoxy, or R$^3$ and R$^4$ together with the nitrogen atom form a 5- or 6-membered saturated or unsaturated heterocyclic ring having zero, one, or two more heteroatoms selected from nitrogen, oxygen, or sulfur, which is substituted by furan, thiophene, pyrrole, imidazole, pyridine, or pyrimidine, which is optionally mono- or disubstituted by methyl, fluorine, chlorine, bromine, hydroxy, —CF$_3$, or methoxy, or the pharmacologically acceptable acid addition salts, solvates, and hydrates thereof.

6. The compound of formula 1 according to claim 5, wherein:

R$^1$ and R$^2$, which are identical or different, are each a methyl or ethyl group optionally substituted by cyclopropyl, hydroxy, or fluorine, or R$^1$ and R$^2$ together are a C$_3$–C$_4$-alkylene bridge;

R$^3$ is hydrogen or C$_1$–C$_3$-alkyl optionally substituted by hydroxy, fluorine, or —CF$_3$; and R$^4$ is C$_1$–C$_3$-alkyl optionally substituted by hydroxy, fluorine, or —CF$_3$, or R$^4$ is a phenyl group optionally substituted by one or two groups selected from furyl, thienyl, phenyl, or phenyl mono-, di-, or trisubstituted by methyl, fluorine, bromine, hydroxy, —CF$_3$, or methoxy, or R$^4$ is a benzyl group optionally substituted at the phenyl ring by one, two, or three groups selected from methyl, ethyl, hydroxy, fluorine, chlorine, bromine, —CF$_3$, methoxy, furyl, thienyl, or phenyl, or R$^4$ is a benzyl group optionally substituted at the methylene bridge by one, two, or three groups selected from methyl, ethyl, hydroxy, fluorine, chlorine, bromine, —CF$_3$, methoxy, or phenyl, or R$^4$ is a group of formula

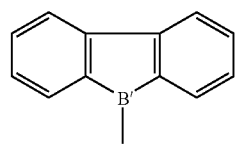

wherein B' is CH optionally mono- or disubstituted by one or more groups selected from methyl, fluorine, chlorine, bromine, hydroxy, —CF$_3$, or methoxy, or the pharmacologically acceptable acid addition salts, solvates, and hydrates thereof.

7. The compound of formula 1 according to claim 6, wherein:

R$^4$ is C$_1$–C$_3$-alkyl optionally substituted by hydroxy, fluorine, or —CF$_3$; or R$^4$ is a phenyl group optionally substituted by phenyl optionally mono- or disubstituted by methyl, fluorine, hydroxy, or —CF$_3$, or R$^4$ is a benzyl group optionally substituted at the phenyl ring by one or two groups selected from methyl, ethyl, hydroxy, fluorine, —CF$_3$, or phenyl, or R$^4$ is a benzyl group optionally monosubstituted at the methylene bridge by phenyl, or R$^4$ is a group of formula

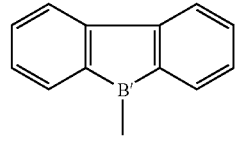

wherein B' is CH optionally mono- or disubstituted by one or more groups selected from methyl, fluorine, chlorine, bromine, hydroxy, —CF$_3$, or methoxy, or the pharmacologically acceptable acid addition salts, solvates, and hydrates thereof.

8. The compound of formula 1 according to one of claims 1 to 4, wherein R$^1$ and R$^2$ are each methyl, or the pharmacologically acceptable acid addition salts, solvates, and hydrates thereof.

9. The compound of formula 1 according to claim 5, wherein R$^1$ and R$^2$ are each methyl, or the pharmacologically acceptable acid addition salts, solvates, and hydrates thereof.

10. The compound of formula 1 according to claim 6, wherein R$^1$ and R$^2$ are each methyl, or and the pharmacologically acceptable acid addition salts, solvates, and hydrates thereof.

11. The compound of formula 1 according to claim 7, wherein R$^1$ and R$^2$ are each methyl, or the pharmacologically acceptable acid addition salts, solvates, and hydrates thereof.

12. The compound of formula 1 according to one of claims 1 to 4, wherein $R^3$ is hydrogen or methyl, or the pharmacologically acceptable acid addition salts, solvates, and hydrates thereof.

13. The compound of formula 1 according to claim 5, wherein $R^3$ is hydrogen or methyl, or the pharmacologically acceptable acid addition salts, solvates, and hydrates thereof.

14. The compound of formula 1 according to claim 6, wherein $R^3$ is hydrogen or methyl, or the pharmacologically acceptable acid addition salts, solvates, and hydrates thereof.

15. The compound of formula 1 according to claim 7, wherein $R^3$ is hydrogen or methyl, and the pharmacologically acceptable acid addition salts, solvates, or hydrates thereof.

16. The compound of formula 1 according to one of claims 1 to 4, wherein $R^4$ is biphenyl, benzyl, fluorenyl, or biphenylmethyl, or the pharmacologically acceptable acid addition salts, solvates, and hydrates thereof.

17. The compound of formula 1 according to claim 5, wherein $R^4$ is biphenyl, benzyl, fluorenyl, or biphenylmethyl, or the pharmacologically acceptable acid addition salts, solvates, and hydrates thereof.

18. The compound of formula 1 according to claim 6, wherein $R^4$ is biphenyl, benzyl, fluorenyl, or biphenylmethyl, or the pharmacologically acceptable acid addition salts, solvates, and hydrates thereof.

19. The compound of formula 1 according to claim 7, wherein $R^4$ is biphenyl, benzyl, fluorenyl, or biphenylmethyl, or the pharmacologically acceptable acid addition salts, solvates, and hydrates thereof.

20. The compound of formula 1 according to claim 1, wherein:

A is

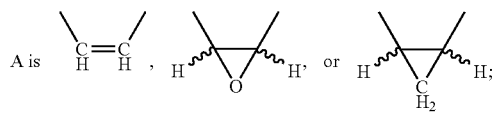

$X^-$ is bromide or methanesulfonate;
$R^1$ and $R^2$ are each methyl;
$R^3$ is hydrogen or methyl; and
$R^4$ is biphenyl, benzyl, fluorenyl, or biphenylmethyl, or the pharmacologically acceptable acid addition salts, solvates, and hydrates thereof.

21. A compound of formula 4

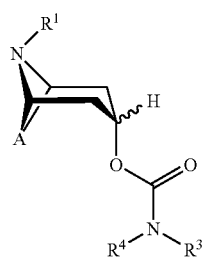

wherein:

A is

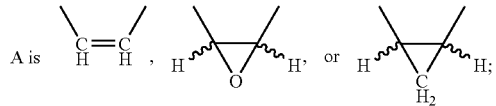

$R^1$ is $C_1$–$C_5$-alkyl optionally substituted by $C_3$–$C_6$-cycloalkyl or hydroxy, or $R^1$ is —$C_3$–$C_5$-alkylene-X, wherein X is chloride, bromide, iodide, sulfate, phosphate, methanesulfonate, nitrate, maleate, acetate, citrate, fumarate, tartrate, oxalate, succinate, benzoate, or p-toluenesulfonate; and $R^3$ and $R^4$, which are identical or different, are each:
(a) hydrogen, or
(b) $C_1$–$C_5$-alkyl optionally mono- or polysubstituted by one or more groups selected from hydroxy, halogen, —$CF_3$, or —$OC_1$–$C_4$-alkyl, or
(c) a $C_2$–$C_5$-alkenyl or $C_2$–$C_5$-alkynyl group, each optionally mono- or polysubstituted by one or more groups selected from hydroxy, halogen, —$CF_3$, —$OC_1$–$C_4$-alkyl, phenyl, or phenyl mono- or polysubstituted by methyl, halogen, hydroxy, —$CF_3$, or methoxy, or
(d) $C_6$–$C_{10}$-aryl optionally substituted by one or more groups selected from $C_1$–$C_4$-alkyl, hydroxy, fluorine, bromine, —$CF_3$, —$OC_1$–$C_4$-alkyl, phenyl, or phenyl mono- or polysubstituted by methyl, fluorine, bromine, hydroxy, —$CF_3$, or methoxy, or
(e) $C_6$–$C_{10}$-aryl substituted by a 5- or 6-membered heteroaryl ring optionally mono- or polysubstituted by methyl, halogen, hydroxy, —$CF_3$, or methoxy, or
(f) $C_6$–$C_{10}$-aryl-$C_1$–$C_4$-alkylene optionally substituted at the aryl group by one or more groups selected from $C_1$–$C_4$-alkyl, hydroxy, halogen, —$CF_3$, —$OC_1$–$C_4$-alkyl, phenyl, or phenyl mono- or polysubstituted by methyl, halogen, hydroxy, —$CF_3$, or methoxy, or
(g) $C_6$–$C_{10}$-aryl-$C_1$–$C_4$-alkylene substituted at the aryl group by a 5- or 6-membered heteroaryl ring optionally mono- or polysubstituted by methyl, halogen, hydroxy, —$CF_3$, or methoxy, or
(h) $C_6$–$C_{10}$-aryl-$C_1$–$C_4$-alkylene optionally substituted at the alkylene group by one or more groups selected from $C_1$–$C_4$-alkyl, hydroxy, halogen, —$CF_3$, —$OC_1$–$C_4$-alkyl, or phenyl, or
(i) a 5- or 6-membered saturated or unsaturated ring having one, two, or three heteroatoms selected from nitrogen, oxygen, or sulfur, and which is optionally mono- or polysubstituted by one or more groups selected from $C_1$–$C_4$-alkyl hydroxy, halogen, —$CF_3$, phenyl, benzyl, or —$OC_1$–$C_4$-alkyl, or
(j) a 5- or 6-membered saturated or unsaturated ring having one, two, or three heteroatoms selected from nitrogen, oxygen, or sulfur, and which is substituted by a 5- or 6-membered heteroaryl ring, which is optionally mono- or polysubstituted by methyl, halogen, hydroxy, —$CF_3$, or methoxy, or
(k) $C_3$–$C_6$-cycloalkyl optionally substituted by one or more groups selected from $C_1$–$C_4$-alkyl, hydroxy, halogen, —$CF_3$, —$OC_1$–$C_4$-alkyl, phenyl, or phenyl mono- or polysubstituted by methyl, halogen, hydroxy, —$CF_3$, or methoxy, or
(l) $C_3$–$C_6$-cycloalkyl substituted by a 5- or 6-membered heteroaryl ring optionally mono- or polysubstituted by methyl, halogen, hydroxy, —$CF_3$, or methoxy, or
(m) a group of formula

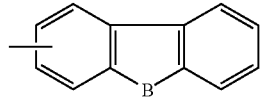

wherein B is —$CH_2$—, —NH—, —S—, or —O—, which is optionally mono- or polysubstituted by one or more groups selected from $C_1$–$C_4$-alkyl, hydroxy, halogen, —$CF_3$, or —$OC_1$–$C_4$-alkyl, or (n) a group of formula

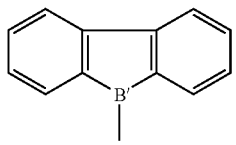

wherein B' is CH or N, which is optionally mono- or polysubstituted by one or more groups selected from $C_1$–$C_4$-alkyl, hydroxy, halogen, —$CF_3$, or —$OC_1$–$C_4$-alkyl, or (o) a group of formula

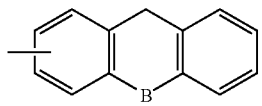

wherein B is —$CH_2$—, —NH—, —S—, or —O—, which is optionally mono- or polysubstituted by one or more groups selected from $C_1$–$C_4$-alkyl, hydroxy, halogen, —$CF_3$, or —$OC_1$–$C_4$-alkyl, or (p) a group of formula

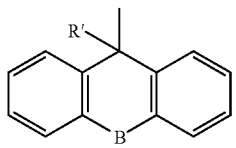

wherein B is —$CH_2$—, —NH—, —S—, or —O—, and

R' is hydrogen, hydroxy, methyl, hydroxymethyl, ethyl, —$CF_3$, —$CHF_2$, or halogen, and which is optionally mono- or polysubstituted by one or more groups selected from $C_1$–$C_4$-alkyl, hydroxy, halogen, —$CF_3$, or —$OC_1$–$C_4$-alkyl, or $R^3$ and $R^4$ together with the nitrogen atom form a 5- or 6-membered saturated or unsaturated heterocyclic ring having zero, one, or two more heteroatoms selected from nitrogen, oxygen, or sulfur, and which is optionally mono- or polysubstituted by one or more groups selected from $C_1$–$C_4$-alkyl hydroxy, halogen, —$CF_3$, phenyl, benzyl, or —$OC_1$–$C_4$-alkyl, or $R^3$ and $R^4$ together with the nitrogen atom form a 5- or 6-membered saturated or unsaturated heterocyclic ring substituted by a 5- or 6-membered heteroaryl ring, which is optionally mono- or polysubstituted by methyl, halogen, hydroxy, —$CF_3$, or methoxy, and the acid addition salts, solvates, and hydrates thereof, with the proviso that if A is

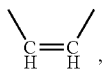

$R^1$ is methyl, and $R^3$ is hydrogen, $R^4$ cannot be phenyl, pentafluorophenyl, or cyclopentyl; and with the proviso that if A is

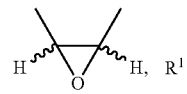

$R^1$ is methyl, and $R^3$ is hydrogen, $R^4$ cannot be phenyl.

22. The compound of formula 4 according to claim 21, wherein:

$R^1$ is $C_1$–$C_3$-alkyl optionally substituted by $C_3$–$C_5$-cycloalkyl, hydroxy, or fluorine, or $R^1$ is $C_3$–$C_4$-alkylene-X, wherein X is chloride, bromide, methanesulfonate, or p-toluenesulfonate;

$R^3$ and $R^4$, which are identical or different, are each:
 (a) hydrogen, or
 (b) $C_1$–$C_5$-alkyl optionally substituted by hydroxy, fluorine, —$CF_3$, or methoxy, or
 (c) a phenyl or naphthyl group optionally substituted by one, two, or three groups selected from methyl, ethyl, hydroxy, fluorine, bromine, —$CF_3$, methoxy, phenyl, or phenyl mono-, di-, or trisubstituted by methyl, fluorine, chlorine, bromine, hydroxy, —$CF_3$, or methoxy, or
 (d) a phenyl or naphthyl group, each substituted by furan, thiophene, pyrrole, imidazole, pyridine, or pyrimidine, which is optionally mono- or disubstituted by methyl, fluorine, bromine, hydroxy, —$CF_3$, or methoxy, or
 (e) a benzyl or phenylethyl group, each optionally substituted at the phenyl ring by one, two, or three groups selected from methyl, ethyl, hydroxy, fluorine, chlorine, bromine, —$CF_3$, methoxy, phenyl, or phenyl mono-, di-, or trisubstituted by methyl, fluorine, chlorine, bromine, hydroxy, —$CF_3$, or methoxy, or
 (f) a benzyl or phenylethyl group, each substituted at the phenyl ring by furan, thiophene, pyrrole, imidazole, pyridine, or pyrimidine, which is optionally mono- or disubstituted by methyl, fluorine, chlorine bromine, hydroxy, —$CF_3$, or methoxy, or
 (g) a benzyl or phenylethyl group, each optionally substituted at the alkylene bridge by one or two groups selected from methyl, ethyl, hydroxy, fluorine, chlorine, bromine, —$CF_3$, methoxy, or phenyl, or
 (h) a 5- or 6-membered saturated or unsaturated ring having one, two, or three heteroatoms selected from nitrogen, oxygen, or sulfur, and which is optionally mono-, di-, or trisubstituted by one or more groups selected from methyl, ethyl, hydroxy, fluorine, chlorine, bromine, —$CF_3$, phenyl, benzyl, and methoxy, or
 (i) a 5- or 6-membered saturated or unsaturated ring having one, two, or three heteroatoms selected from nitrogen, oxygen, or sulfur, and which is substituted by furan, thiophene, pyrrole, imidazole, pyridine, or pyrimidine, which is optionally mono- or disubstituted by methyl, fluorine, chlorine, bromine, hydroxy, —$CF_3$, or methoxy, or
 (l) a cyclopentyl or cyclohexyl group, each optionally substituted by one, two, or three groups selected from methyl, ethyl, hydroxy, fluorine, chlorine, bromine, —$CF_3$, methoxy, phenyl, or phenyl mono-, di-, or trisubstituted by methyl, fluorine, chlorine, bromine, hydroxy, —$CF_3$, or methoxy, or
 (k) a cyclopentyl or cyclohexyl group, each substituted by furan, thiophene, pyrrole, imidazole, pyridine, or pyrimidine, which is optionally mono- or disubstituted by methyl, fluorine, chlorine, bromine, hydroxy, —CF$_3$, or methoxy, or (l) a group of formula

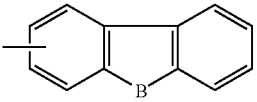

wherein B is —CH$_2$', —NH—, —S—, or —O—, which is optionally mono-, di-, or trisubstituted by one or more groups selected from methyl, fluorine, chlorine, bromine, hydroxy, —CF$_3$, or methoxy, or (m) a group of formula

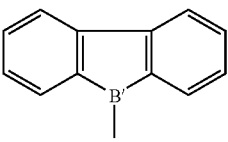

wherein B' is CH or N, which is optionally mono-, di-, or trisubstituted by one or more groups selected from methyl, fluorine, chlorine, bromine, hydroxy, —CF$_3$, or methoxy, or (n) a group of formula

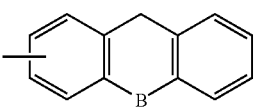

wherein B is —CH$_2$—, —NH—, —S—, or —O—, which is optionally mono-, di-, or trisubstituted by one or more groups selected from methyl, fluorine, chlorine, bromine, hydroxy, —CF$_3$, or methoxy, or (o) a group of formula

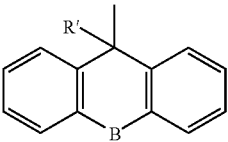

wherein B is —CH$_2$—, —NH—, —S—, or —O—, and

R' is hydrogen, hydroxy, methyl, hydroxymethyl, ethyl, —CF$_3$, —CHF$_2$, or fluorine, and which is optionally mono-, di-, or trisubstituted by one or more groups selected from methyl, fluorine, chlorine, bromine, hydroxy, —CF$_3$, and methoxy, or R$^3$ and R$^4$ together with the nitrogen atom form a 5- or 6-membered saturated or unsaturated heterocyclic ring having zero, one, or two more heteroatoms selected from nitrogen, oxygen, or sulfur, and which is optionally mono-, di-, or trisubstituted by methyl, fluorine, chlorine, bromine, hydroxy, phenyl, —CF$_3$, or methoxy, or R$^3$ and R$^4$ together with the nitrogen atom form a 5- or 6-membered saturated or unsaturated heterocyclic ring having zero, one, or two more heteroatoms selected from nitrogen, oxygen, or sulfur, which is substituted by furan, thiophene, pyrrole, imidazole, pyridine, or pyrimidine, which is optionally mono- or disubstituted by methyl, fluorine, chlorine bromine, hydroxy, —CF$_3$, or methoxy, and the acid addition salts, solvates, and hydrates thereof, with the proviso that if A is

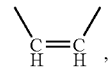

R$^1$ is methyl, and R$^3$ is hydrogen, R$^4$ cannot be phenyl, 2-chloro-4-trifluoromethylphenyl, 3-chloro-4-methoxyphenyl, or cyclopentyl; and with the proviso that if A is

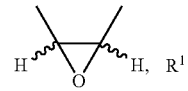

R$^1$ is methyl, and R$^3$ is hydrogen, R$^4$ cannot be phenyl.

23. The compound of formula 4 according to claim 22, wherein:

R$^1$ is a methyl or ethyl group, each optionally substituted by cyclopropyl, hydroxy, or fluorine, or R$^1$ is C$_3$–C$_4$-alkylene-X, wherein X is chloride, bromide, methanesulfonate, or p-toluenesulfonate;

R$^3$ is hydrogen or C$_1$–C$_3$-alkyl optionally substituted by hydroxy, fluorine, or —CF$_3$;

R$^4$ is C$_1$–C$_3$-alkyl optionally substituted by hydroxy, fluorine, or —CF$_3$, or R$^4$ is a phenyl group optionally substituted by one or two groups selected from furyl, thienyl, phenyl, or phenyl mono-, di-, or trisubstituted by methyl, fluorine, bromine, hydroxy, —CF$_3$, or methoxy, or R$^4$ is a benzyl group optionally substituted at the phenyl ring by one, two, or three groups selected from methyl, ethyl, hydroxy, fluorine, chlorine, bromine, —CF$_3$, methoxy, furyl, thienyl, or phenyl, or R$^4$ is a benzyl group optionally substituted at the methylene bridge by one, two, or three groups selected from methyl, ethyl, hydroxy, fluorine, chlorine, bromine, —CF$_3$, methoxy, or phenyl, or R$^4$ is a group of formula

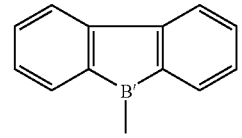

wherein B' is CH optionally mono- or disubstituted by one or more groups selected from methyl, fluorine, chlorine, bromine, hydroxy, —CF$_3$, or methoxy, and the acid addition salts, solvates, and hydrates thereof, with the proviso that if A is

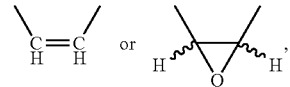

R$^1$ is methyl, and R$^3$ is hydrogen, R$^4$ cannot be phenyl.

24. The compound of formula 4 according to claim 23, wherein:

$R^1$ is a methyl or ethyl group, each optionally substituted by cyclopropyl, hydroxy, or fluorine, or $R^1$ is $C_3$–$C_4$-alkylene-X, where X is chloride, bromide, methanesulfonate, and p-toluenesulfonate;

$R^3$ is hydrogen or $C_1$–$C_3$-alkyl optionally substituted by hydroxy, fluorine, or —$CF_3$;

$R^4$ is $C_1$–$C_3$-alkyl optionally substituted by hydroxy, fluorine, or —$CF_3$, or $R^4$ is a phenyl group optionally substituted by phenyl optionally mono- or disubstituted by methyl, fluorine, hydroxy, or —$CF_3$, or $R^4$ is a benzyl group optionally substituted at the phenyl ring by one or two groups selected from methyl, ethyl, hydroxy, fluorine, —$CF_3$, or phenyl, or $R^4$ is a benzyl group optionally monosubstituted by phenyl at the methylene bridge, or $R^4$ is a group of formula

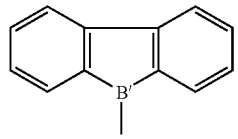

wherein B' is CH optionally mono- or disubstituted by one or more groups selected from methyl, fluorine, chlorine, bromine, hydroxy, —$CF_3$, or methoxy, and the acid addition salts, solvates, and hydrates thereof, with the proviso that if A is

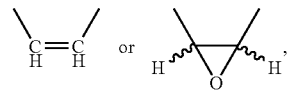

$R^1$ is methyl, and $R^3$ is hydrogen, $R^4$ cannot be phenyl.

25. The compound of formula 4 according to claim 24, wherein:

$R^1$ is methyl;

$R^3$ is hydrogen or methyl; and $R^4$ is biphenyl, benzyl, fluorenyl, or biphenylmethyl, and the acid addition salts, solvates, and hydrates thereof.

26. A pharmaceutical composition comprising an effective amount of a compound of formula 1 according to one of claims 1 to 4 or a pharmacologically acceptable acid addition salt, solvate, or hydrate thereof, or a pharmaceutically acceptable excipient or carrier.

* * * * *